United States Patent
Kovarik

(10) Patent No.: US 10,842,834 B2
(45) Date of Patent: *Nov. 24, 2020

(54) METHOD AND SYSTEM FOR REDUCING THE LIKELIHOOD OF DEVELOPING LIVER CANCER IN AN INDIVIDUAL DIAGNOSED WITH NON-ALCOHOLIC FATTY LIVER DISEASE

(71) Applicant: Joseph E. Kovarik, Englewood, CO (US)

(72) Inventor: Joseph E. Kovarik, Englewood, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/722,117

(22) Filed: Dec. 20, 2019

(65) Prior Publication Data

US 2020/0121743 A1    Apr. 23, 2020

Related U.S. Application Data

(63) Continuation-in-part of application No. 16/229,252, filed on Dec. 21, 2018, now Pat. No. 10,512,661, which is a continuation-in-part of application No. 15/392,173, filed on Dec. 28, 2016, now Pat. No. 10,245,288.

(60) Provisional application No. 62/275,341, filed on Jan. 6, 2016.

(51) Int. Cl.
| | |
|---|---|
| *A61K 35/747* | (2015.01) |
| *A61K 9/00* | (2006.01) |
| *A61K 35/742* | (2015.01) |
| *A61K 35/745* | (2015.01) |

(52) U.S. Cl.
CPC ............ *A61K 35/747* (2013.01); *A61K 9/006* (2013.01); *A61K 35/742* (2013.01); *A61K 35/745* (2013.01)

(58) Field of Classification Search
None
See application file for complete search history.

(56) References Cited

U.S. PATENT DOCUMENTS

| | | |
|---|---|---|
| 3,178,341 A | 4/1965 | Hamill et al. |
| 3,832,460 A | 8/1974 | Kosti |
| 4,136,162 A | 1/1979 | Fuchs et al. |
| 4,568,639 A | 2/1986 | Lew |
| 4,687,841 A | 8/1987 | Spilburg et al. |
| 4,720,486 A | 1/1988 | Spilburg et al. |
| 4,995,555 A | 2/1991 | Woodruff |
| 5,002,970 A | 3/1991 | Eby, III |
| 5,277,877 A | 1/1994 | Jeffrey et al. |
| 5,614,501 A | 3/1997 | Richards |
| 5,719,196 A | 2/1998 | Uhari |
| 6,054,143 A | 4/2000 | Jones |
| 6,139,861 A | 10/2000 | Friedman |
| 6,210,699 B1 | 4/2001 | Acharya |
| 6,287,610 B1 | 9/2001 | Bowling et al. |
| 6,569,474 B2 | 5/2003 | Clayton et al. |
| 6,599,883 B1 | 7/2003 | Romeo |
| 6,722,577 B2 | 4/2004 | Dobyns, III |
| 6,919,373 B1 | 7/2005 | Lam et al. |
| 7,087,249 B2 | 8/2006 | Burrell |
| 7,267,975 B2 | 9/2007 | Strobel et al. |
| 7,353,194 B1 | 4/2008 | Kerker et al. |
| 7,540,432 B2 | 6/2009 | Majerowski et al. |
| 7,820,420 B2 | 10/2010 | Whitlock |
| 7,862,808 B2 | 1/2011 | Isolauri et al. |
| 7,901,925 B2 | 3/2011 | Bojrab |
| 8,034,606 B2 | 10/2011 | Park et al. |
| 8,197,872 B2 | 6/2012 | Mills et al. |
| 8,349,313 B2 | 1/2013 | Smith et al. |
| 8,420,074 B2 | 4/2013 | Rehberger et al. |
| 8,454,729 B2 | 6/2013 | Mittelmark et al. |

(Continued)

FOREIGN PATENT DOCUMENTS

| | | |
|---|---|---|
| WO | PCT/US2008/080362 | 4/2009 |
| WO | WO 2011/020780 | 2/2011 |
| WO | WO 2013/026000 | 2/2013 |
| WO | WO 2011/029701 | 5/2013 |
| WO | WO 2013/107750 | 7/2013 |
| WO | PCT/US2014/036849 | 5/2014 |

OTHER PUBLICATIONS

Malaguarnera et al. (Dig Dis Sci, 57:545-553, 2012).

*Primary Examiner* — Brian Gangle
(74) *Attorney, Agent, or Firm* — Sheridan Ross P.C.

(57) ABSTRACT

A method for reducing the likelihood of developing liver cancer in an individual diagnosed with non-alcoholic fatty liver disease involves providing in the gut of an individual a population of beneficial bacteria selected from the group consisting of *Lactobacillus* species, and administering fiber to the individual to maintain a therapeutically effective amount of the beneficial bacteria in the gut of the individual. In certain embodiments, monoacylglycerolacyltransferase-3 (MGAT3) synthesis is inhibited to lower triacylglycerol (TAG) production, while in others, expression of diacylglycerolacyltransferase-2 (DGAT-2) is inhibited. The beneficial bacteria are preferably modified to produce increased amounts of butyrate and may also be encapsulated in a frangible enclosure. Levels of *Roseburia* are preferably increased while the levels of *Akkermansia* spp. in the individual's gut microbiome are reduced. In other embodiments, a therapeutically effective amount of a bacterial formulation comprising *Faecalibacterium prausnitzii* is administered, or a composition comprising modified *L. reuteri* bacteria having the ability to survive conditions in the duodenum or jejunum of the individual's small intestine. Other embodiments include the administration of a bacterial formulation comprising at least one of *Coprococcus, Veillonella, Roseburia, Bifidobacterium, Faecalibacterium prausnitzii* and *Prevotella*.

20 Claims, 1 Drawing Sheet

(56) References Cited

U.S. PATENT DOCUMENTS

| | | |
|---|---|---|
| 8,481,299 B2 | 7/2013 | Gueniche |
| 8,496,914 B2 | 7/2013 | Bonfiglio |
| 8,585,588 B2 | 11/2013 | Kovarik et al. |
| 8,685,389 B2 | 4/2014 | Baur |
| 8,701,671 B2 | 4/2014 | Kovarik |
| 8,716,327 B2 | 5/2014 | Zhao |
| 8,758,764 B2 | 6/2014 | Masignani et al. |
| 8,815,538 B2 | 8/2014 | Lanzalaco et al. |
| 8,865,211 B2 | 10/2014 | Tzannis |
| 8,945,839 B2 | 2/2015 | Zhang |
| 8,951,775 B2 | 2/2015 | Castiel |
| 8,999,372 B2 | 4/2015 | Davidson |
| 9,011,834 B1 | 4/2015 | McKenzie et al. |
| 9,017,718 B2 | 4/2015 | Tan |
| 9,028,841 B2 | 5/2015 | Henn et al. |
| 9,131,884 B2 | 9/2015 | Holmes |
| 9,234,204 B2 | 1/2016 | Qvit-Raz et al. |
| 9,288,981 B2 | 3/2016 | Gandhi et al. |
| 10,245,288 B2 | 4/2019 | Kovarik |
| 10,512,661 B2 | 12/2019 | Kovarik |
| 2003/0031737 A1 | 2/2003 | Rosenbloom |
| 2003/0206995 A1 | 11/2003 | Bowling et al. |
| 2004/0053352 A1 | 3/2004 | Ouyang et al. |
| 2004/0096569 A1 | 5/2004 | Barkalow et al. |
| 2004/0115223 A1 | 6/2004 | Follansbee |
| 2004/0120991 A1 | 6/2004 | Schobel |
| 2004/0142463 A1 | 7/2004 | Walker et al. |
| 2004/0166501 A1 | 8/2004 | Azimzai et al. |
| 2004/0228804 A1 | 11/2004 | Jones et al. |
| 2005/0118655 A1 | 6/2005 | Weinstock et al. |
| 2005/0196358 A1 | 9/2005 | Georglades et al. |
| 2006/0035008 A1 | 2/2006 | Virgalli et al. |
| 2006/0252087 A1 | 11/2006 | Tang et al. |
| 2007/0054008 A1 | 3/2007 | Clayton et al. |
| 2007/0057086 A1 | 3/2007 | Van Kippersluis |
| 2007/0059718 A1 | 3/2007 | Toner et al. |
| 2007/0059774 A1 | 3/2007 | Grisham et al. |
| 2007/0063026 A1 | 3/2007 | Mamaropolos et al. |
| 2007/0087020 A1 | 4/2007 | O'Connor |
| 2007/0207955 A1 | 9/2007 | Tanihara et al. |
| 2007/0218114 A1 | 9/2007 | Sorousch |
| 2007/0231923 A1 | 10/2007 | Cumberland et al. |
| 2008/0112983 A1 | 5/2008 | Bufe et al. |
| 2008/0267933 A1 | 10/2008 | Ohlson et al. |
| 2008/0305089 A1 | 12/2008 | Bufe et al. |
| 2009/0196907 A1 | 8/2009 | Bunick |
| 2009/0196908 A1 | 8/2009 | Lee |
| 2009/0205083 A1 | 8/2009 | Gupta et al. |
| 2010/0029832 A1 | 2/2010 | Pinnavaia et al. |
| 2010/0260720 A1 | 10/2010 | Sprenger |
| 2010/0285098 A1 | 11/2010 | Haley |
| 2011/0142942 A1 | 6/2011 | Gardner et al. |
| 2011/0217368 A1 | 9/2011 | Prakash et al. |
| 2012/0027786 A1 | 2/2012 | Gupta |
| 2012/0029832 A1 | 2/2012 | Dodgson |
| 2012/0039806 A1 | 2/2012 | Lahoud et al. |
| 2012/0058094 A1 | 3/2012 | Blasser et al. |
| 2012/0128597 A1 | 5/2012 | Peters et al. |
| 2012/0142548 A1 | 6/2012 | Corsi et al. |
| 2012/0276143 A1 | 11/2012 | O'Mahony et al. |
| 2012/0276525 A1 | 11/2012 | Kovarik et al. |
| 2013/0059815 A1 | 3/2013 | Fournell et al. |
| 2013/0157876 A1 | 6/2013 | Lynch et al. |
| 2013/0259834 A1 | 10/2013 | Klaenhammer et al. |
| 2013/0315869 A1 | 11/2013 | Qimron et al. |
| 2013/0323025 A1 | 12/2013 | Crawford et al. |
| 2013/0323100 A1 | 12/2013 | Poulton et al. |
| 2013/0326645 A1 | 12/2013 | Cost et al. |
| 2013/0330215 A1 | 12/2013 | Li |
| 2014/0044677 A1 | 2/2014 | Qvit-Raz et al. |
| 2014/0045744 A1 | 2/2014 | Gordon |
| 2014/0065209 A1 | 3/2014 | Putaala et al. |
| 2014/0065218 A1 | 3/2014 | Lang et al. |
| 2014/0066817 A1 | 3/2014 | Kovarik et al. |
| 2014/0068797 A1 | 3/2014 | Doudna et al. |
| 2014/0154290 A1 | 6/2014 | Peters et al. |
| 2014/0199266 A1 | 7/2014 | Park |
| 2014/0238411 A1 | 8/2014 | Kovarik |
| 2014/0255351 A1 | 9/2014 | Berstad et al. |
| 2014/0271867 A1 | 9/2014 | Myers |
| 2014/0333003 A1 | 11/2014 | Allen |
| 2014/0349405 A1 | 11/2014 | Sontheimer et al. |
| 2014/0356460 A1 | 12/2014 | Lutin |
| 2014/0363441 A1 | 12/2014 | Grandea, III et al. |
| 2014/0377278 A1 | 12/2014 | Elinav et al. |
| 2015/0017227 A1 | 1/2015 | Kim |
| 2015/0064138 A1 | 3/2015 | Lu et al. |
| 2015/0071957 A1 | 3/2015 | Kelly |
| 2015/0086581 A1 | 3/2015 | Li et al. |
| 2015/0093473 A1 | 4/2015 | Barrangou |
| 2015/0132263 A1 | 5/2015 | Liu et al. |
| 2015/0150792 A1 | 6/2015 | Klingman |
| 2015/0166641 A1 | 6/2015 | Goodman |
| 2015/0190435 A1 | 7/2015 | Henn et al. |
| 2015/0216917 A1 | 8/2015 | Jones |
| 2015/0252358 A1 | 9/2015 | Maeder |
| 2015/0329555 A1 | 11/2015 | Liras |
| 2015/0329875 A1 | 11/2015 | Gregory |
| 2015/0352023 A1 | 12/2015 | Berg |
| 2015/0353901 A1 | 12/2015 | Liu |
| 2015/0361436 A1 | 12/2015 | Hitchcock |
| 2015/0374607 A1 | 12/2015 | Lanzalaco et al. |
| 2016/0008412 A1 | 1/2016 | Putaala et al. |
| 2016/0040216 A1 | 2/2016 | Wilder |
| 2016/0089315 A1 | 3/2016 | Kleinberg et al. |
| 2016/0089405 A1 | 3/2016 | Lue |
| 2016/0151427 A1 | 6/2016 | Whitlock et al. |
| 2016/0168594 A1 | 6/2016 | Zhang et al. |
| 2016/0199424 A1 | 7/2016 | Berry et al. |
| 2016/0206564 A1 | 7/2016 | Trachtman |
| 2016/0213702 A1 | 7/2016 | Von Maltzahn et al. |
| 2016/0271189 A1 | 9/2016 | Cutcliffe |
| 2016/0314281 A1 | 10/2016 | Apte |
| 2018/0000878 A1 | 1/2018 | Goodman et al. |
| 2018/0207165 A1 | 7/2018 | Harmsen et al. |
| 2018/0296582 A1 | 10/2018 | Von Maltzahn et al. |
| 2018/0312851 A1 | 11/2018 | Falb et al. |
| 2018/0326008 A1 | 11/2018 | Schreiber et al. |

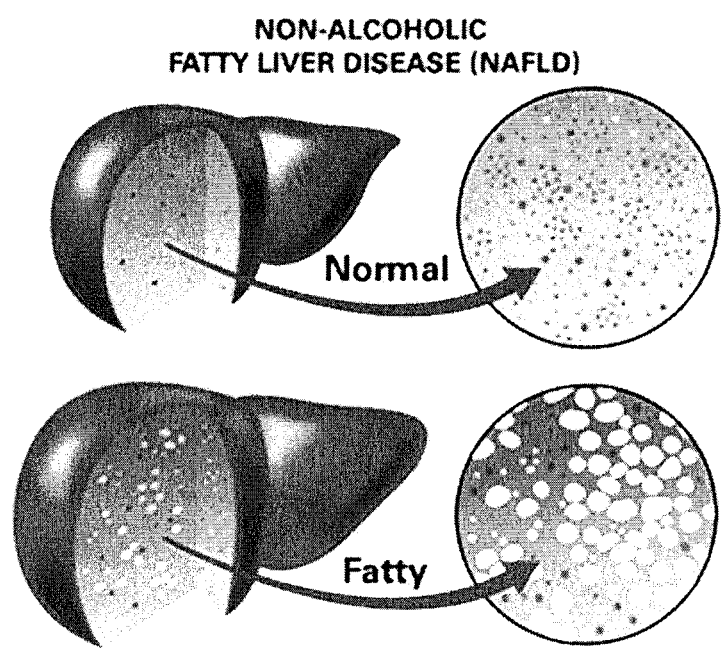

METHOD AND SYSTEM FOR REDUCING THE LIKELIHOOD OF DEVELOPING LIVER CANCER IN AN INDIVIDUAL DIAGNOSED WITH NON-ALCOHOLIC FATTY LIVER DISEASE

RELATED APPLICATIONS

This application is a continuation-in-part of U.S. patent application Ser. No. 16/229,252, filed Dec. 21, 2018 (now U.S. Pat. No. 10,512,661, issued Dec. 24, 2019), which is a continuation-in-part of U.S. patent application Ser. No. 15/392,173, filed Dec. 28, 2016 (now U.S. Pat. No. 10,245,288, issued Apr. 2, 2019), which is a non-provisional of U.S. Provisional Patent Application Ser. No. 62/275,341, filed on Jan. 6, 2016.

The entire disclosure of the prior applications are considered to be part of the disclosure of the accompanying application and are hereby incorporated by reference.

FIELD OF THE INVENTION

The present invention is directed to a method for reducing the likelihood of developing non-alcoholic steatohepatitis (NASH) in an individual diagnosed with non-alcoholic fatty liver disease involves providing in the gut of an individual a population of beneficial bacteria selected from the group consisting of *Lactobacillus* species, and at least 6 grams per day of fiber to the individual to maintain a therapeutically effective amount of the beneficial bacteria in the gut of the individual. In certain embodiments, monoacylglycerolacyltransferase-3 (MGAT3) synthesis is inhibited to lower triacylglycerol (TAG) production, while in others, expression of diacylglycerolacyltransferase-2 (DGAT-2) is inhibited. The beneficial bacteria are preferably modified to produce increased amounts of butyrate and are also encapsulated in a frangible enclosure. Levels of *Roseburia* are preferably increased while the levels of *Akkermansia* spp. in the individual's gut microbiome are reduced.

BACKGROUND OF THE INVENTION

The human gut is perhaps one of the most complex networks in the body and is colonized by trillions of microorganisms including bacteria, archaea, fungi, protists, and viruses, among which bacteria are the major inhabitants. Hepatocellular carcinoma (HCC) is one of the most common malignancies in the world. Gut microbiota has been demonstrated to play a critical role in liver inflammation, chronic fibrosis, liver cirrhosis, and HCC development through the gut-liver axis. Gut microbial dysbiosis accompanies the progression of alcoholic liver disease, non-alcoholic fatty liver disease and liver cirrhosis, and promotes HCC progression. Microbial dysbiosis contributes to cancer susceptibility via multiple pathways. Further studies have suggested that the microbiota and their associated metabolites are not only closely related to carcinogenesis by inducing inflammation and immune dysregulation, which lead to genetic instability, but also interfere with the pharmacodynamics of anticancer agents. Chronic inflammation has been verified as a driving cause of cancer. Inflammation promotes tumor progression and accelerates the invasion and metastasis. The generation of inflammation-associated factors can also inactivate tumor-suppressor genes (e.g., P53 mutation). The hepatic environment is greatly influenced by the pathogens or metabolites produced by the microbiota in the GI tract through the hepatic portal venous system. Liver exerts an essential effect on the host microbial community by filtering the blood stream as well as metabolizing and neutralizing toxins derived from intestinal microbes. Gut microbial dysbiosis contributes to hepatocarcinogenesis because the microbiota and microbial metabolites are detected by liver resident immune cells and are able to modify hepatic metabolism. NAFLD is considered to be a major risk factor for HCC.

Microbial community in *H. pylori*-positive individuals is characterized by an increase in the counts of Proteobacteria, Spirochaetes, and Acidobacteria, as well as a decrease in the counts of Actinobacteria, Bacteroidetes, and Firmicutes. *H. pylori* generally inhabits the human stomach. However, *H. pylori* from the gut can reach the liver tissue through the blood stream of the portal vein after surviving phagocytic elimination, or by reverse migration via the duodenum. Tight junctions of gut epithelium get degraded due to chronic inflammation. As a result, there is an increase in intestinal permeability, as well as bacterial counts and the levels of metabolites translocated from the gut epithelium into circulation because of the chronic inflammation.

NAFLD is the new pandemic of the twenty first century, co-existing with obesity. Fatty liver is caused by an abnormality in liver metabolism that results in the accumulation of fat. It can be seen as a consequence of metabolic deregulation associated with energy surplus and exceeded reservoir ability of adipose tissue to store fat/energy. NAFLD is strongly associated with obesity, insulin resistance (IR)/type 2 diabetes mellitus (T2DM) and the metabolic syndrome. Obesity, particularly central obesity, is highly predictive of hepatic steatosis and disease progression, being directly proportional to the increase of body mass index (BMI). More than two third of patients with type-2 diabetes have NAFLD.

NAFLD is also associated with increased overall mortality and particularly increased cardiovascular mortality. It is increasing worldwide, paralleling the obesity pandemic. It has been estimated that about one billion individuals worldwide have NAFLD. In the Western and in the Asian world, one third of the population is affected. NAFLD is presently the third cause of liver transplantation in the United States and is increasing at a rate such that it will be the first cause in the next few years.

NAFLD is the most common liver complication of irritable bowel syndrome and also affects people with ulcerative colitis and Crohn's disease. NAFLD has become the leading cause of chronic liver diseases worldwide, causing considerable liver-related mortality and morbidity. During the past decade, it has also become increasingly evident that NAFLD is a multisystem disease that affects many extra-hepatic organ systems, including the heart and the vascular system.

Non-alcoholic fatty liver disease is a condition ranging from benign lipid accumulation in the liver (steatosis) to steatosis combined with inflammation. The latter is referred to as non-alcoholic steatohepatitis (NASH). NASH is viewed as the hepatic component of metabolic syndrome. Estimates from the USA are that 5.7% to 17% of all adults have NASH, while 17% to 33% of Americans have NAFLD. As obesity and insulin resistance reach epidemic proportions in industrialized countries, the prevalence of both NAFLD and NASH is increasing and is therefore considered to be a major health hazard. Steatosis alone is considered a relatively benign condition for the liver itself and is also a reversible condition. However, the transition towards NASH represents a key step in the pathogenesis, as it sets the stage for further damage to the liver, such as fibrosis, cirrhosis and liver cancer. While the mechanisms leading to steatosis are well described, little is known about the actual risk factors that drive hepatic inflammation during the progression to NASH. Consequently, therapeutic options are poor.

The number one cause of death in patients with NAFLD is cardiovascular disease, followed by malignancies and then liver disease. Despite huge amounts of money spent on investigating its origins and prevention, there is presently no effective treatment for NAFLD. There is no clear curative treatment for NAFLD and thus, the management of patients is directed to controlling of co-morbidities known to promote not only liver disease, but also cardiovascular disease and overall mortality. At present, individuals diagnosed with NAFLD are treated by focusing on diet and exercise, in order to lose weight. Weight loss of 5% or more of body weight results in a NAFLD remission rate of 75%. In addition, recommendations are to have cholesterol intake lowered to 200 mg per day, whole grains emphasized and high fructose corn syrup avoided. Higher fructose consumption, in the form of soft drinks, has been associated with NAFLD as it is believed to promote bacterial overgrowth and hence increases the load of endotoxin that reaches the liver. Some studies have shown a possible beneficial effect in NAFLD for very mild alcohol consumption. Coffee has also been shown to have a protective effect in terms of metabolic control and NAFLD development and progression. The effect of lipid lowering agents in NAFLD is still not completely understood, though some studies have suggested a mild benefit in the use of statins. The accumulation of specific lipid intermediates, including DAG, acyl-CoA, and ceramide is thought to drive the progression of NAFLD in humans.

Existing treatments for NAFLD demonstrate various deficiencies. For example, available drugs such as vitamin E, pioglitazone, and pentoxifylline have borderline efficacy, but are limited by potential side-effects and toxicities, and do not improve liver fibrosis. Weight gain is common in patients taking thiazolidinediones, and these drugs can cause fluid retention and precipitate congestive heart failure. Rosiglitazone use is also associated with increased risk of myocardial infarction.

A genetic link to NAFLD has been studied but has not been found. NAFLD is more frequent in East Asian Indians, followed by Hispanics, Asians, Caucasians and less frequent in African Americans. While such racial disparities are not fully understood, it is known that African Americans have lower fructose absorption rates than Hispanics, and fructose is considered an important driver of liver steatogenesis.

The gastrointestinal tract harbors an abundant and diverse microbial community. It is a complex system, providing an environment or niche for a community of many different species or organisms, including diverse strains of bacteria. Hundreds of different species may form a commensal community in the GI tract in a healthy person, and this complement of organisms evolves from the time of birth to ultimately form a functionally mature microbial population.

A healthy microbiota provides the host with multiple benefits, including colonization resistance to a broad spectrum of pathogens, essential nutrient biosynthesis and absorption, and immune stimulation that maintains a healthy gut epithelium and an appropriately controlled systemic immunity. In settings of 'dysbiosis' or disrupted symbiosis, microbiota functions can be lost or deranged, resulting in increased susceptibility to pathogens, altered metabolic profiles, or induction of proinflammatory signals that can result in local or systemic inflammation or autoimmunity.

Long-chain-length hydrophobic acyl residues play a vital role in a multitude of essential biological structures and processes. Amongst other functions, they build the inner hydrophobic layers of biological membranes, are converted to intracellular storage compounds, and are used to modify protein properties or function as membrane anchors. Metabolic syndrome is an ever-increasing health problem among the world's population. It is a group of intertwined maladies that includes obesity, hypertriglyceridemia, hypertension, nonalcoholic fatty liver disease and diabetes mellitus type II (T2D).

There is a long felt but unsolved need for an effective treatment for NAFLD and the present invention is directed to a solution for this chronic and expanding disease.

SUMMARY OF THE INVENTION

One aspect of the present invention relates to the use of various *Lactobacillus* species to reduce LDL, cholesterol, and triglycerides to cause an improvement and amelioration of inflammation and steatosis. The present inventors believe that particular modulation of the gut microbiome, including the establishment and maintenance of certain beneficial bacteria, including *Lactobacillus, Bifidobacterium*, and certain *Streptococcus* species, forms the basis of a treatment of NAFLD, as well as NASH, and in particular, the use of particular species that have been modified via a CRISPR system. Nonalcoholic steatohepatitis (NASH) is a more advanced form of NAFLD where liver injury has occurred, and can lead to liver failure, portal hypertension, hepatocarcinoma and cirrhosis. Even without significant changes in BMI, glucose, or LDL2, probiotic use is believed to significantly decrease ALT, AST, total cholesterol, HDL, and TNF-$\alpha$1.

Thus, in various embodiments of the present invention, the employment of particular probiotics as described herein, provides a treatment for NAFLD that shows improvements in intestinal dysbiosis, leading to decreasing intestinal permeability, endotoxemia and subsequent inflammation.

The most frequent cause which leads to obesity is a dysbalance between energy intake and energy expenditure. The gut microbiota contributes to host metabolism. Gut microbiota not only influence absorption and disposal of nutrients to the liver, but also can lead to the development of "metabolic endotoxemia" and activation of TLR ligands, which can stimulate liver cells to produce proinflammatory cytokines, thereby initiating inflammation and fibrogenesis, which characterize NASH. Another possible molecular mechanism implicated in NAFLD development is the alteration in LPS-endocannabinoid (eCB) system regulatory loops and bile acid metabolism. Thus, certain embodiments of the present invention are directed to the modification of intestinal bacterial flora by specific probiotics to achieve a therapeutic approach for the treatment of NAFLD.

One strategy for NAFLD treatment encompassed by the present invention relates to a treatment for obesity that involves manipulation of an individual's gut microbiota. Thus, modulation of gut microbiota by probiotic treatment or dietary intervention provides beneficial effects with respect to body weight, influence on glucose and fat metabolism, insulin sensitivity and reduction in chronic systemic inflammation, all of which can impact the status of NAFLD. Probiotic positive effects on host metabolism are specifically directed to beneficial levels of *Lactobacillus* and/or *Bifidobacterium* strains. For example, employment of *Saccharomyces cerevisiae* var. *boulardii, Enterobacter halii* or *Akkermansia muciniphila* are used to achieve beneficial effects for obesity and NAFLD. In certain embodiments, because obstructive sleep apnea and attendant fatigue are common in patients with NAFLD, one aspect of the present invention relates to the use of "no-snore strips" as described herein (and in more extensive pending patent applications incorporated herein by this reference, e.g. U.S. Pat. No. 9,445,936) such that use of such strips can beneficially modify not only the populations of oral bacteria, but also snoring patterns, thus providing those suffering from NAFLD with a way to manage such condition to permit them to address fatigue issues and to thus sleep better, exercise more, etc.

Gut bacteria alter the way individuals store fat, how levels of glucose are balanced in the blood, and how humans respond to hormones that make individuals feel hungry or full. Certain population mixes of microbes set the stage for NAFLD, obesity and diabetes. The gut community in lean people is diverse while obese people have a gut microbe community that is comparatively less diverse. Lean individuals, for example, tended to have a wider variety of Bacteroidetes, a population of varied microbes that specialize in breaking down bulky plant starches and fibers into shorter molecules that the body can use as a source of energy.

Probiotics have physiologic functions that contribute to the health of gut microbiota, can affect food intake and appetite, body weight and composition and metabolic functions through gastrointestinal pathways and the modulation of the gut bacterial community. Thus, in various embodiments of the present invention, probiotics are employed, e.g. (*Enterococcus faecium, Streptococcus thermophilus L. acidophilus, Bifidobacterium longum, L. plantarum* and/or *B. lactis*) to significantly reduce total serum cholesterol and LDL cholesterol and to improve the LDL:HDL cholesterol ratio. In particular embodiments, a CRISPR-Cas system (Clustered Regularly Interspaced Short Palindromic Repeats-CRISPR-associated) is employed to alter one or more of these bacteria to modify various virulence factors associated with bacteria so that beneficial populations of bacteria inhabit an individual's oral and/or gut microbiome.

Various embodiments of the present invention relate to a composition capable of increasing the level of anti-oxidized low-density-lipoprotein (OxLDL) antibodies in vivo for use in the treatment or prevention of NASH. OxLDL is an immunogenic molecule that stimulates the induction of anti-oxLDL antibodies. Phosphorylcholine, a component of *Streptococcus pneumoniae*, is a major antigen in oxLDL, which is recognized by anti-oxLDL antibodies that have protective properties. One embodiment relates to the expression of OxLDL in bacteria via employment of a CRISPR-Cas system to insert genes for OxLDL such that such modified bacteria produce OxLDL to therefore stimulate the induction of anti-oxLDL antibodies, thus providing the protective effects of such antibodies. Using the present invention, fibrosis can be decreased or prevented by the production and administration of anti-oxLDL antibodies to avoid inflammation of the liver and to therefore treat NASH and NAFLD. While antibodies against oxLDL are known in the art, various embodiments of the present invention relate to a new medical use of such antibodies, as well as to methods and systems that modify gut bacteria to enhance the production of such antibodies. In other words, various embodiments of the invention relate to a composition comprising antibodies against oxLDL for use in the treatment or prevention of hepatic inflammation or more in particular treatment or prevention of NASH, and/or the use of oxLDL antibodies for the preparation of a medicament for the treatment or prevention of hepatic inflammation and in the treatment of NASH. In certain embodiments, a method of treatment or prevention of hepatic inflammation is provided where oxLDL antibody levels are increased by modification of particular bacteria using a Clustered Regularly Interspaced Short Palindromic Repeats-CRISPR-associated system (CRISPR-Cas) or Clustered Regularly Interspaced Short Palindromic Repeats from *Prevotella* and *Francisella* 1 (CRISPR/Cpf1) system so that the bacteria is able to produce desired levels of oxLDL anti-bodies.

In other embodiments, the methods and systems disclosed herein are directed to modifying the gut microbiota of an individual to ameliorate the progression of NAFLD, including reducing liver aminotransferases, total-cholesterol, TNF-α and improving insulin resistance in individuals with NAFLD. In certain embodiments, NAFLD is thus treated by modulation of the gut microbiota. Effective treatments include employing a method of populating a subject's gastrointestinal tract with a diverse and useful selection of microbiota in order to alter a dysbiosis. Various aspects and embodiments of the invention are directed to methods and compositions for modulation of NAFLD of an individual's gut microbiome by using bacteria that have been treated with a CRISPR-Cas or CRISPR-Cpf1 system to reverse antibiotic resistance or to render ineffective certain virulence factors in pathogenic bacterial cell, as well as modifying gut bacteria in a manner to make them "better" in various ways, including an ability to outcompete other undesired bacteria. Other various embodiments of the present invention relate to the employment of engineered autonomously distributed circuits containing programmable nucleases (e.g. "programmable nuclease circuits") that are delivered to microbial organisms in vivo to modulate the expression of certain antibiotic resistant and virulence factors of particular microbial organisms. Some embodiments employ the Type II CRISPR-Cas (Clustered Regularly Interspaced Short Palindromic Repeats-CRISPR-associated) system of *Streptococcus pyogenes* to reverse antibiotic resistance in a wide range of microbial organisms. In certain embodiments, the CRISPR-Cas system is used to weaken resistance of microbial pathogens to existing antibiotics. The use of the CRISPR-Cas system may be viewed as a paradigm shift in combating pathogens because it enables autonomous and distributed neutralization of disease at the gene level. Various aspects of the present disclosure provide methods that comprise modifying bacterial cells to target a gene or nucleotide sequence of interest, and in particular, genes involved in the storage of fat. Such modified bacterial cells include an engineered autonomously distributed circuit having at least one nucleic acid encoding a programmable nuclease that targets a gene or nucleotide sequence directed to fat metabolism.

While there are medications approved for treating diseases and conditions associated with NAFLD, there are currently no medications specifically approved for the treatment of NAFLD itself. Treatment protocols have instead been focused upon the associated conditions, such as the metabolic syndrome. Conventional treatment of NAFLD includes weight loss, restricting dietary fat, administration of medications employed in the treatment of an associated condition and administration of medications employed in the treatment of hyperlipidemia. Many medications employed to treat conditions associated with NAFLD are hepatotoxic.

Various embodiments of the present invention are directed to a method for treating NAFLD in a subject in need thereof that includes administering a composition including a therapeutically effective amount of *Prevotella*, and more preferably *Prevotella* that has been modified, e.g. by CRISPR-Cas, in a manner that reduces the effect of at least one of the virulence factors of such bacteria. Other embodiments involve the employment of bacteria of the *Bacteroides* family that have been modified to reduce the amount of a ligand-activated transcription factor.

Dysbiosis in a person's gut has a significant role in the pathogenesis of human NAFLD/NASH. In various embodiments of the present invention, administration of probiotics, as well as associated fiber diets to support such bacteria, is involved, in some embodiments employing *Bifidobacterium* and *Lactobacillus* strains. Control of the bacterial flora lowers proinflammatory cytokine production (tumor necrosis factor-α, interleukin-6, interferon-γ) via down-regulation of the nuclear factor kappa B, and decreases oxidative stress. Probiotics can reduce the urease activity of bacterial microflora, decrease fecal pH value and reduces amino-acid fermentation and ammonia adsorption; reduce aminotransferases, and improve the lipid status in NAFLD patients. Each of these may be modified via CRISPR-Cas systems employed to alternative characteristics of an individual's microbiome.

Microbiome research in liver disease has evolved recently as an exciting new field. Prebiotics encompass products that promote the growth of beneficial intestinal microbiota. Probiotics include live microbial strains in predefined quantities. Both prebiotics and the use of probiotics is involved in the various embodiments of the invention as herein described. The present invention is directed in various embodiments directed to ways to modify the microbiota to treat hepatic steatosis, liver inflammation, fibrosis, and developing and advanced liver disease. The purposeful manipulation of the gut microbiota is done to address various liver diseases at both early and late disease stages.

More than 90% of the adult microbiome is composed of species belonging to four bacterial phyla: Firmicutes, Bacteroidetes, Actinobacteria, and Proteobacteria. Differences exist, however, with respect to different individuals as well as in different habitats. For example, Firmicutes are the major species in the intestine, vagina, skin, and oral cavity, while Actinobacteria and Proteobacteria are more dominant in the oral cavity, skin, and nasal cavity. The enterotype is a classification of the microbiome, with the gut microbiome being classified into three enterotypes. Each enterotype includes a dominant species selected from the group consisting of: *Bacteroides, Prevotella*, and *Ruminococcus*, with enterotypes being unrelated to race, residential region, or diet.

The prevalence of nonalcoholic fatty liver disease (NAFLD) overall is lower in Asia than in Western countries. Urban areas in India and other parts of Asia that have adapted a 'Western' diet report prevalence rates for NAFLD and NASH of 10-24 and 3-4%, respectively, which is similar to their prevalence rates in the West. In addition, the prevalence of NAFLD in an obese population was similarly high in Asia and Western countries. Thus, differences in NAFLD etiology and prevalence are more closely related to dietary patterns than geographic differences.

It is believed that commensal microbiota protect against biliary injury and liver fibrosis. The present inventor believes that there is a significant association of fatty liver with *H. pylori* infection. Thus, various embodiments involve the modification of an individual's microbiome, including *H. pylori* in one's stomach, to combat NAFLD and NASH. Thus use of CRISPR-Cas to render *H. pylori* more susceptible to particular antibiotics is one way in which such modification may be achieved.

NAFLD is a complex disease and a treatment targeting one pathological process often also causes changes in other pathways. Prebiotics represent a specific type of dietary fiber that when fermented, mediate measurable changes within the gut microbiota composition, usually causing an increase in the relative abundance of bacteria thought of as beneficial, such as bifidobacteria or certain butyrate producers. Prebiotics are usually non-digestible carbohydrates, oligosaccharides or short polysaccharides, including inulin, oligofructose, galactofructose, galacto-oligosaccharides and xylo-oligosaccharides, all leading to increasing the relative abundance of bifidobacteria and lactobacilli. The gut of individuals with various maladies, including obesity, harbor bacteria in their gut that establishes an inflammation-associated microbiome, often providing a lower potential for butyrate production and reduced bacterial diversity. Thus, one objective of the present invention is to alter the microbiome of such individuals to increase bacterial diversity in their gut and to increase levels of butyrate production. Patients with NAFLD have small intestinal bacterial overgrowth and increased intestinal permeability. Thus, altering the microbiome of such individuals is achieved to counter the progression of NAFLD. In certain embodiments, one objective is to increase the proportion of *Ruminococcaceae* in a person's microbiome and to also reduce the proportion of *Escherichia*, e.g. by modifying *Escherichia* via CRISPR-Cas to make it less viable than it otherwise would be.

Probiotics can reduce liver aminotransferases, total cholesterol, tumor necrosis factor α and improve insulin resistance in patients with NAFLD. Similarly, treatment of other diseases in the gut, like inflammatory bowel disease (IBD) is implicated with respect to modification of the gut microbiome. The concept of an altered gut microbiota or dysbiosis is possibly the most significant development in IBD and NAFLD research in the past decade. A definitive change of the normal gut microbiota with a breakdown of host-microbial mutualism is believed to be the defining event in IBD and NAFLD development.

In other embodiments, one objective is to increase the levels of *Lactobacillus, Leuconostoc, Lactococcus, Pediococcus* and Firmicutes in an individual's gut microbiome, while reducing the levels of Bacteroidetes and *Akkermansia* spp. In certain other embodiments, one objective is to increase the levels of *Prevotella* and *Roseburia* (a butyrate-producer) in a person's gut microbiome, and especially the colon microbiome. Other embodiments focus on increasing the levels of *Bacteroides* in the person's gut and decreasing the levels of *Escherichia, Lachnospiraceae* and *Megasphaera*.

Periodontal disease is a chronic infectious disease of the tissues surrounding the teeth that result in tooth loss. Several reports have indicated that periodontal infection is related to NAFLD. Both NAFLD and periodontal disease are chronic inflammatory conditions that are known as 'silent diseases'. Therefore, both conditions need to be detected early and treated under collaborative medical and dental care in order to prevent progression to NASH. The prevalence of NAFLD in the American general adult population is 10%-40% and that of NASH is approximately 2%-5%. One aspect of the present invention is directed to the relationship between periodontal pathogens, e.g. composed of *P. gingivalis*, and the severity of NAFLD. The eradication of periodontal pathogens, such as *P. gingivalis* infection, is believed to have a beneficial effect upon NASH.

Certain embodiments of the present invention are directed to a method for treating non-alcoholic fatty liver disease by providing to an individual in need thereof an effective amount of a composition comprising modified *L. reuteri* bacteria, preferably using CRISPR-Cas and/or Cpf1 systems, to provide such bacteria in a manner so that they have the ability to survive the conditions in the duodenum or jejunum of the small intestine. Other embodiments involve a method for treating non-alcoholic fatty liver disease involving establishing in the gut of an individual a population of beneficial bacteria selected from the group consisting of *Lactobacillus, Bifidobacterium*, and *Streptococcus* species and administering at least 6 grams per day of fiber to the individual to maintain the beneficial bacteria in the gut of the individual. Still other embodiments are directed to a method for treating non-alcoholic fatty liver disease by increasing oxLDL antibody levels in an individual by modifying bacteria, preferably using a CRISPR-Cas or Cpf1 system, so that the bacteria is able to produce desired levels of oxLDL. Yet other methods involve the modulation of NAFLD of an individual's gut microbiome by using beneficial bacteria, e.g. such as one or more of bacteria from one or more of the phylas: Firmicutes, Bacteroidetes, Actinobacteria, and Proteobacteria, preferably treated with a CRISPR-Cas or CRISPR-Cpf1 system to reverse antibiotic resistance or to render ineffective certain virulence factors in pathogenic bacterial cells. In other embodiments, an individual is administered a therapeutically effective amount of *Prevotella*, and more preferably *Prevotella* that has been modified in a manner that reduces the effect of at least one of the virulence factors of such bacteria. Certain embodiments are directed to a method for treating non-alcoholic fatty liver disease involving the modifying of bacteria of the *Bacteroides* family so that they produce reduced amounts of a ligand-activated transcription factor as compared to non-modified bacteria. In preferred embodiments, probiotics are further provided to feed such bacteria, with the result being improvements in levels of density lipoprotein, and tumor necrosis factor-α.

The growth of microbiota communities is under control of distinct subfamilies of host genes encoding antimicrobial peptides (AMPs). When bacteria colonize a given human habitat, the expression of AMPs, including .alpha. and .beta. defensins and cathelicidins, is upregulated in order to limit the spreading of bacteria. The equilibrium between the immune system and immunoregulatory functions of bacteria appears to be a delicate balance in which the loss of a specific species can lead to an overreaction or suppression of the innate immune system. The maintenance of a stable, fermentative gut microbiota requires diets rich in whole plant foods particularly high in dietary fibers and polyphenols. Individuals colonized by bacteria of the genera *Faecalibacterium, Bifidobacterium, Lactobacillus, Coprococcus*, and *Methanobrevibacter* have significantly less of a tendency to develop obesity-related diseases like type-2-diabetes and ischemic cardiovascular disorders. These species are characterized by high production of lactate, propionate and butyrate as well as higher hydrogen production rates, which are known to inhibit biofilm formation and activity of pathogens. Thus, in various embodiments of the present invention, these bacterial species are selected and administered to an individual in preferred ratios that reflect those of healthy individuals so as to attain the general balance of bacterial populations in a person's gut. Moreover, preferably bacteria are selected that are effective in inhibiting biofilm formation and in particular, those that demonstrate a high production of lactate, propionate, butyrate and hydrogen. CRISPR-Cas and/or Cpf1 may be employed to provide such characteristics to the selected bacterial species in this regard.

One will appreciate that this Summary of the Invention is not intended to be all encompassing one of skill in the art will appreciate that the entire disclosure, as well as the incorporated references, provides a basis for the scope of the present invention as it may be claimed now and in future applications.

BRIEF DESCRIPTION OF THE DRAWINGS

FIG. 1 is an illustration depicting the visual difference in appearance between a normal liver and a liver with non-alcoholic fatty liver disease.

DETAILED DESCRIPTION OF PREFERRED EMBODIMENTS

Probiotic therapies can reduce liver aminotransferases, total-cholesterol, TNF-α and improve insulin resistance in NAFLD patients. Modulation of the gut microbiota represents a new treatment for NAFLD. In certain embodiments, the methods and systems as described herein are directed to inhibiting glucosphingolipid synthesis in an individual by provision of particular microbes effective to achieve such inhibition. In other embodiments, an engineered autonomously distributed circuit that contains a programmable nuclease able to target a virulence factor or an antibiotic resistance gene of the bacterial species is employed, whether they be Gram-negative bacterial cells, Gram-positive bacterial cells, or a combination thereof. Microbial cells may include members of the phyla Actinobacteria, Bacteroidetes, Proteobacteria, Firmicutes, or a combination thereof. In particular embodiments, gut bacteria are modified to address the synthesis of triacylglycerol. There is a direct correlation between high triacylglycerol (triglyceride; TAG) levels and the severity of metabolic syndrome. Thus, controlling the synthesis of TAG will have a great impact on overall systemic lipid metabolism and thus metabolic syndrome progression.

The Acyl-CoA: monoacylglycerolacyltransferase (MGAT) family has three members (MGAT1, -2, and -3) that catalyze the first step in TAG production, conversion of monoacylglycerol (MAG) to diacylglycerol (DAG). TAG is then directly synthesized from DAG by a Acyl-CoA: diacylglycerolacyltransferase (DGAT). The conversion of MAG→DAG→TAG is the major pathway for the production of TAG in the small intestine, and produces TAG to a lesser extent in the liver.

One aspect of various embodiments of the present invention is directed towards the therapeutic potential of inhibiting MGAT for lowering TAG synthesis. Elevated plasma TAG has been associated with an increased risk of coronary and cerebrovascular ischemic events. Excessive TAG synthesis in the intestine due to dietary fat absorption followed by increased accumulation of TAG in the liver and adipose plays an integral role in the progression of metabolic disorders including obesity, insulin resistance, T2D, and fatty liver disease. Limiting TAG production in humans provides a way to address these metabolic disorders.

TAG is de novo synthesized in the liver and adipose tissue, while dietary TAG is broken down and re-synthesized in the small intestine. In the liver, TAG is used for very low density lipoprotein (VLDL) assembly. Newly formed VLDL is secreted into the circulatory system where it transports neutral lipids including TAG to peripheral tissues. In the small intestine, dietary TAG is hydrolyzed by pancreatic lipase to FA and MAG that are re-absorbed in the intestinal lumen. Enterocytes then re-synthesize TAG and secrete it as ApoB-containing chylomicrons that deliver dietary fat to tissues. Most tissues including liver and adipose use the G3P pathway for the synthesis of TAG. In contrast, the small intestine predominately relies on the MAG pathway.

MGAT is a major regulator of TAG homeostasis in response to diet. In humans, the expression of MGATs is up-regulated in the livers of insulin-resistant patients who have nonalcoholic fatty liver disease (NAFLD). MGAT has related acyltransferases (DGAT) and they share similar molecular relationships, however, MGAT genes share homology with DGAT2 and not DGAT1. DGAT1 is mainly expressed in adipose and small intestine tissues; DGAT2 is expressed in liver tissue. There exists a fundamental role for DGAT2 in TAG biosynthesis, much more so than DGAT1.

There presently are very few therapeutics existing to treat NAFLD. Various aspects of the present invention relate to the inhibition of MGAT2 to lower TAGs and to also reduce or eliminate the progression of NAFLD, which ultimately progresses to NASH, and later cirrhosis. In certain embodiments, protection of the liver from developing NASH involves the inhibition of MGAT2 synthesis (rather than MGMAT1). Thus, various embodiments of the present invention are directed to the protection of the liver from developing NASH by effective inhibition of MGAT2 synthesis by employing bacteria of an individual's microbiome, especially using bacteria modified via CRISPR-Cas systems to achieve inhibition of MGAT2 synthesis.

In still other embodiments, protection of the liver from developing NASH involves the inhibition of MGAT3 synthesis. The MGAT3 gene, Mogat3, exists only in higher mammals and not in rodents. Thus, employment of bacterial systems, especially engineered gut microbes that carry inhibitors of Mogat3, is one method and system to achieve the treatment, likelihood of prevention and the prevention of NAFLD. The sequence of MGAT3 is more homologous to DGAT2 than to MGAT1 or MGAT2. Thus, MGAT3 exhibits significantly higher DGAT activity than MGAT1 and MGAT2. MGAT3 expression levels increase in patients with NAFLD and its levels decrease after gastric bypass surgery-induced weight loss. It is therefore believed that MGAT3 plays a more important role than MGAT2 in obesity related hepatic insulin resistance and NAFLD progression in humans. In various embodiments of the present invention either the expression of MGAT2 or MGAT3, or both, is employed to combat NAFLD, and in particular, via the employment of modified gut bacteria via enhancement of such expression by use of the CRISPR-Cas/Cpf1 systems as described herein.

While the inhibition of human intestinal DGAT enzyme blocks TAG synthesis completely and has led to severe fat malabsorption, the use of DGAT1 inhibitors as anti-diabetes and/or anti-obesity agents is not favored due to gastrointestinal side effects. One aspect of the present invention is directed to achieving the reduction of TAG synthesis without these gastrointestinal side effects.

In human liver tissue, MGAT2/MGAT3 expression is correlated with the progression of NAFLD. In the small intestine, MGAT2 inhibition results in changes in TAG absorption and synthesis, as well as incretin secretion. These actions contribute to weight loss, improvement of insulin sensitivity and hypertriglyceridemia, and the prevention of NAFLD progression. While the blocking of dietary TAG absorption using inhibitors to DGAT1 exhibit unwanted gastrointestinal side effects, the targeting of the MAG pathway as a therapeutic for metabolic syndrome is a viable option for inhibiting intestinal TAG synthesis without such side effects. Inhibition of intestinal MGAT2 results in dynamic changes in TAG and cholesterol absorption, which leads to the changes in systemic energy balance and gut incretin release. Inhibition of the MGAT2 isozyme in the liver improves steatosis by attenuating fat accumulation and insulin resistance. In adipose, MGAT2 inhibition reduces fat biosynthesis and improves glucose uptake. Thus, one aspect of the present invention relates to either or both MGAT3 and MGAT2 inactivation in various tissues, especially by employing modified gut bacteria as described herein, to achieve the benefits of reducing body weight, improving insulin resistance, decreasing hyperlipidemia, and attenuating hepatic steatosis.

Acyl-CaA:diacylglycerol acyltransferase (DGAT) catalyzes the final step in triglyceride synthesis by facilitating the linkage of sn-1,2 diacylglygerol (DAG) with a long chain acyl CoA. There are two primary isoforms of DGAT, DGAT-1 and DGAT-2. DGAT-1 is primarily expressed in the small intestine while DGAT-2 exhibits primarily hepatic expression where its expression is insulin responsive. Inhibiting expression of DGAT-2 significantly improves hepatic steatosis. Thus, the materials and methods of various embodiments of the present invention can be used to alter expression of DGAT-2 for the treatment of NASH and NALFD, and to reduce hepatic insulin resistance. While certain aspects of the present invention can involve the use of engineered nucleases to knock out DGAT-2 in a subset of liver cells, or involve the use of an engineered transcription factor that can be used to down-regulate DGAT-2 expression, other more preferred treatment methods employ the use of CRISPR-Cas or Cpf1 systems to inhibit DGAT-2 expression.

In still other embodiments, the present invention is directed to addressing primary sclerosing cholangitis (PSC), a disease that involves severe inflammation and scarring that develops in the bile ducts and is associated with patients who suffer from IBD. Those with PSC may ultimately require liver transplantation. The cause is not known and there is no effective medication for PSC. Primary biliary cirrhosis is a chronic inflammatory intrahepatic liver disorder that slowly destroys the small-to-medium-sized bile ducts within the liver. When these ducts are damaged, bile builds up in the liver (cholestasis) and over time damages liver tissue. Primary sclerosing cholangitis is a similar, but affects the part of the bile duct that is outside of the liver. In both diseases, inflammation leads to progressive thickening, scarring, and destruction of the bile ducts. The buildup of bile, bile salts, and cholesterol in the liver causes damage to cell membranes in the liver, reduced production of bile salts, and fibrosis (development of scar tissue). Fibrosis is both a marker of liver damage and a potential contributor to liver failure. Continuing damage causes scarring or cirrhosis of the liver (the liver slowly deteriorates and malfunctions), and prevents proper liver function and impaired blood circulation in the intestines. While not bound by theory, these diseases are believed to be autoimmune diseases and the present inventor believes that modulation of a person's gut microbiota can avoid the development of such autoimmunity, thus providing a treatment and method of preventing PBC and PSC. It is believed that bacterial antigens translocate across a leaky and possibly inflamed gut wall into the portal and biliary system to induce an abnormal immune response and contribute to primary sclerosing cholangitis pathogenesis.

In various embodiments, the focus of modification of an individual's microbiome is directed to the microbiome of the small intestine, while in others it is directed to the colon, and in still others, to both. One strategy in the treatment of NAFLD is to ameliorate or turn off inflammatory triggers, with some of the main targets including cytokines such as tumor necrosis factor (TNF)-α, chemokines, TLR4, and the NLRP3 inflammasome. Gut microorganism-derived bacterial products including endotoxin (lipopolysaccharide), peptidoglycan, and bacterial DNA can travel up the portal vein to activate TLR4 and TLR9 on Kupffer cells and other hepatic cell types. In turn, this activation can lead to the release of cytokines and chemokines that promote NASH. In still other embodiments, modulation of particular bacteria by CRISPR-Cas and Cpf1 systems, for example, to address bacterial pyruvate dehydrogenase complex component E2 (PDC-E2) homologues in particular bacteria, including but not limited to E. coli, Novosphingobium aromaticivorans, Mycobacterium and Lactobacillus species, are used to effectively treat and/or prevent these diseases. There is believed to be a common core gut microbial response to chronic inflammation and immune activation, such as observed in type 2 diabetes.

In yet other embodiments of the present invention, the present inventors submit that bacterial expression of RNA molecules can be employed to generate miRNA molecules that interact with the human host mRNA during bacterial infection. Thus, such micro-RNAs derived from bacterial RNAs are used to regulate gene expression of the human host cell involved in different human diseases, including NAFLD. Bacterially derived microRNA sequences can significantly regulate the expression of various human genes and thus, enhancing an individual's gut bacteria by employing CRISPR systems to regulate microRNA sequences forms various embodiments of the present invention. In addition to NAFLD, microRNAs are believed to be involved in many human diseases, such as cancer, diabetes, rheumatoid arthritis, and others that respond to a particular bacterial environment, and thus, while the present description is focused on NAFLD, it will be understood that other diseases can similarly be addressed by employment of the systems and methods as described herein.

MicroRNAs (miRNA) are small important regulators of gene expression and are currently believed to regulate approximately 70% of human genes. More than a thousand different miRNA have been characterized in the human genome and they all are assumed to function by a similar mechanism: The miRNAs base-pair with target messenger RNA (mRNA) and recruit nucleases that degrade the targeted RNA from the termini and/or inhibit translation. In cancer and many other diseases, deregulation of gene-expression is observed and in many cases miRNAs have been shown to play an integral part or even the causative role in disease development. According to various embodiments, the present invention concerns a method for the treatment, amelioration or prevention of a disease or medical disorder associated with the presence or over-expression of micro-RNA. Therefore, in certain aspects of the invention, inhibiting miRNA activity is a strategy to treat disease, especially NAFLD.

miRNAs are a class of highly conserved non-coding regulatory factors that negatively regulate more than half of the protein-coding genes in mammals, are essential to most biological processes, including proliferation, differentiation and apoptosis, and their transcription is tightly controlled. In certain embodiments, a CRISPR system and/or a modified CRISPR interference system (CRISPRi) employing inactive Cas9, may be used to reversibly prevent the expression of both monocistronic miRNAs and polycistronic miRNA clusters. Such CRISPR-based systems are reversible and thus provide advantages over more conventional knockdown techniques. The CRISPR/CRISPRi system may be adapted to target a particular miRNA sequence by employing a single repression vector, often entailing using a 20-bp sequence and thus, such a CRISPR/CRISPRi method is useful in the generation of vectors that target multiple miRNAs and with reduced toxicity and can silence miRNAs with no off-target effects. Using such CRISPR systems to silence miRNAs involved in the progression of NAFLD is therefore one focus of particular embodiments of the present invention.

In various embodiments, particular bacterial species are targeted for modification and use to address the treatment of NAFLD. For example, L. reuteri is well-established as one of the most ubiquitous members of the naturally-occurring gut bacteria. Host-specific strains of L. reuteri have been documented to confer broad-spectrum protection from an assortment of microbial and chemical associated disease in humans and animals. However, traditional probiotic therapy involves administration of bacteria with the hope that some bacteria will survive the harsh gastric conditions and colonize the colon where the bacteria will reproduce and live indefinitely. Far fewer bacteria survive in the duodenum, jejunum or ileum because of factors such as acidity, immune response and bile concentration. In certain embodiments, it is believed that bacteria must be present in the duodenum or jejunum of the small intestine for lowering cholesterol and in particular bile acid. Thus, certain aspects of the present invention are directed to the modification of particular bacteria using CRISPR-Cas and/or Cpf1 systems to provide bacteria having the ability to survive the conditions in the duodenum or jejunum of the small intestine. Thus, in one embodiment, CRISPR systems are employed to render certain bacteria adaptive to harsh acid conditions and that are otherwise considered to be beneficial to a person in avoiding fatty liver disease. Highly bile salt hydrolase active bacteria provide an improved agent for reducing serum cholesterol, serum lipids, body fat, and atherogenic index and for prophylaxis and treatment of atherosclerosis, cardiovascular and cerebrovascular diseases. Modification of an individual's gut microbes to render a significant population thereof to have enhanced degrees of BSH characteristics is one objective of various embodiments of the present invention.

Oral administration of probiotics has been shown to significantly reduce cholesterol levels, such cholesterol-lowering effects ascribed to BSH activity. Deconjugated bile salts are less efficiently reabsorbed than their conjugated counterparts, which results in the excretion of larger amounts of free bile acids in feces. Also, free bile salts are less efficient in the solubilization and absorption of lipids in the gut. Therefore, deconjugation of bile salts is believed to lead to a reduction in serum cholesterol either by increasing the demand for cholesterol for de novo synthesis of bile acids to replace those lost in feces or by reducing cholesterol solubility and thereby absorption of cholesterol through the intestinal lumen. Microbial BSHs function in the detoxification of bile salts and in doing so increase the intestinal survival and persistence of producing strains. Thus, one embodiment of the present invention is directed to enhancing the BSH activity by a probiotic bacterium to maximize its prospects of survival in the hostile environment of the gastrointestinal tract. Increased intestinal survival increases the overall beneficial effects associated with strains possessing such BSH enhanced activities. Enhanced BSH activity benefits probiotic bacterium that are able to survive and perform in the intestinal milieu. BSH significantly contributes to bile tolerance and survival and persistence of strains in the intestinal tract. Thus, certain embodiments are directed to the manipulation of bacterial strains to enhance the BSH activity of probiotic strains (either to over express a native BSH or to express or over express a heterologous BSH) to improve their survivability in the intestinal tract. Extraction of fecal bacteria form a person and employing the techniques as described herein on such native populations to enhance various aspects thereof, including for example BSH activity, and then returning such modified gut bacteria to the individual, is one method that may be used to address NAFLD in a positive manner.

This is accomplished in various embodiments by the employment of CRISPR-Cas and Cpf1 systems to insert BSH genes in select bacteria. Certain embodiments include the administration of bile-hydrolyzing strains (especially those modified by CRISPR-Cas and/or Cpf1 systems) to control serum cholesterol. The ingestion of probiotics as described herein is believed to be deemed preferable to statins as a way to achieve a cholesterol-lowering therapy. Manipulation of BSH activity as described herein provides for more robust probiotics (whether delivered orally or via the fecal transplantations as described herein) with improved competitiveness and performance. Statin drugs target many of the underlying inflammatory pathways involved in metabolic syndrome (MetS). Thus, certain embodiments relate to the use of CRISPR-Cas systems to modify bacteria of an individual's microbiome so that they produce effective levels of statin drugs. The metabolic syndrome (MetS) is comprised of a cluster of closely related risk factors, including visceral adiposity, insulin resistance, hypertension, high triglyceride, and low high-density lipoprotein cholesterol; all of which increase the risk for the development of type 2 diabetes and cardiovascular disease. A chronic state of inflammation appears to be a central mechanism underlying the pathophysiology of insulin resistance and MetS. Thus in various embodiments of the present invention, use of probiotics and prebiotics in combination, as described herein, is employed to address the cause of NAFLD, but that is also believed to address related conditions, such as MetS.

In one embodiment, the bacteria employed and that are modified via CRISPR-Cas and Cpf1 to enhance expression of BSH include *Lactobacillus, Bifidobacteria, Pediococcus, Streptococcus, Enterococcus,* or *Leuconostoc*. In another embodiment, the *Lactobacillus* is *Lactobacillus reuteri*, optionally, *Lactobacillus reuteri* (NCIMB 701359), *Lactobacillus reuteri* (NCIMB 701089), *Lactobacillus reuteri* (ATCC 55148), *Lactobacillus reuteri* (ATCC 23272), *Lactobacillus reuteri* (NCIMB 702655), *Lactobacillus reuteri* (LMG 18238), *Lactobacillus reuteri* (CCUG 32271), *Lactobacillus reuteri* (CCUG 32305), *Lactobacillus reuteri* (CCUG 37470), *Lactobacillus reuteri* (CCUG 44001) or *Lactobacillus reuteri* (CCUG 44144). In another embodiment, the *Lactobacillus reuteri* adheres to the gastrointestinal epithelial cells, competes for adhesion, or inhibits the binding of other bacteria due to cell surface proteins.

The human gut is a rich habitat populated by numerous microorganisms, each having a CRISPR system. In certain embodiments, the CRISPR-Cas system may be employed to render certain bacteria sensitized to certain antibiotics such that specific chemical agents can selectively choose those bacteria more susceptible to antibiotics, see, e.g. US Pat. Publication No. 2013/0315869 to Qimron, which is incorporated in its entirety by this reference. Another aspect of certain embodiments includes making synthetic CRISPR-containing RNAs that target genes of interest and using them with Cas enzymes.

In various embodiments, the CRISPR-Cas and or Cpf1 system is employed to control the composition of the gut flora, such as by circumventing commonly transmitted modes of antibiotic resistance and distinguishing between beneficial and pathogenic bacteria. For applications that require the removal of more than one strain, multiple spacers that target shared or unique sequences may be encoded in a single CRISPR array and/or such arrays may be combined with a complete set of cas genes to instigate removal of strains lacking functional CRISPR-Cas/Cpf1 systems. Because of the sequence specificity of targeting, CRISPR-Cas/CPF1 systems may be used to distinguish strains separated by only a few base pairs.

There are ongoing ethical concerns arising with respect to the use of CRISPR-Cas systems—especially as it relates to modification of the human genome. In preferred embodiments of the present invention, however, such issues are much less prevalent for various reasons. First, because preferred embodiments relate to the modification of microbes—rather than to the human genome—and especially those microbes that show tropism for humans, the unintended consequences of employing Crispr-Cas on organisms is lessened, if not eliminated. Moreover, use of CRISPR-Cas to also insert genes that have controllable elements such that the cells are killed by triggering the expression of such genes, is another way to reduce if not eliminate concerns about an unintended release of a modified organism. These types of controls are well known to those of skill in the art and have been long employed, for example, by those involved in creating genetically engineered organisms, such as by inserting genes so that organisms become susceptible to various conditions, such as temperature, antibiotic exposure, etc., such that microbes that may somehow escape desired conditions will not be viable. Modifying the human genome, made possible by the CRISPR technique, has its upsides but also equally daunting downsides. Permanent deletion of genes from the human genome is much more controversial than deletion or modification of bacterial genes. Thus, one desirable aspect of the present invention is directed to the far less controversial modification of gut microbes resident in the human being to promote health and to trigger the desired immune responses as described herein.

In other embodiments, the use of CRISPR-Cas systems is employed to increase butyrate production of select bacteria. For example, *F. prausnitzii*, one of the most abundant species in the colon, is an important producer of butyrate, a major product of carbohydrate fermentation which is implicated in providing protection against colorectal cancer and ulcerative colitis. CRISPR systems are used to enhance the production of butyrate by insertion of genes into select *F. prausnitzii* bacteria to protect against colorectal cancer and other diseases.

Because CRISPR-Cas/Cpf1 acts before transcription occurs, it is able to be employed to target regulatory and other elements on the DNA of microbes that make up a person's gut microbiome. In certain embodiments, CRISPR-Cas may be employed to deliver fluorescent markers to certain DNA sequences, thus permitting one to determine whether any particular sample has been treated in accordance with the present invention, thus ensuring, for example, identity of various materials, compliance with safety issues, effectiveness of gene expression or excision, etc. permitting labeling of living cells with a desired color to discern particular attributes and states.

Other embodiments are focused on diet as it relates to the use of probiotics. The gut microbiota plays a critical role in transforming dietary polyphenols into absorbable biologically active species, acting on the estimated 95% of dietary polyphenols that reach the colon. Certain embodiments rely upon the ability to deliver agents via mucosal adhesive strips, such as described, for example, in U.S. Pat. No.

8,701,671, which is fully incorporated herein by this reference. Thus, in various embodiments of the present invention, the engineering of communal bacteria with improved properties using a CRISPR/Cas system is employed to provide for the enhancement of health, especially as it relates to an individual's microbiome. In certain embodiments the present invention is directed to delivering to microbial cells in vivo a delivery vehicle with at least one nucleic acid encoding a gene or nucleotide sequence of interest, such method employing an RNA-guided nuclease. The microbial cells may be either or both pathogenic microbial cells or non-pathogenic bacterial cells and the gene or nucleotide sequence of interest may be a virulence factor gene, a toxin gene, an antibiotic resistance gene, or a modulatory gene, and most preferably the nucleotide sequence of interest comprises 16S ribosomal DNA (rDNA). In various embodiments, the delivery vehicle is a bacteriophage. Thus, various embodiments of the present invention include the use of CRISPR-Cas, with the recognition that this system can be employed to benefit human health by modifying the bacterial and other microbe communities that humans have long been exposed to in a fashion such that the beneficial aspects of such microbes can be preserved, while the disadvantageous aspects can be "cut out" of the microbe DNA—rather than attempting to change or modify the DNA of a human.

The present invention is one way in which human health concerns can be benefited directly by the use of a DNA deletion system without affecting the long term and permanent deletion of human genes. It is not believed to be obvious, let alone intuitive, that human health can be benefited by such a DNA deletion system used in a fashion that affects only gut microbes in a human's system.

Another aspect of the present invention includes the ability to load or impregnate mucosal strips with any number of active agents to achieve other desirable aspects, such as administration of particular vitamins, medicinal components, and certain CRISPR-Cas modified bacteria. In some embodiments the microbes are encapsulated within encapsulation structures selected to provide the desired degree of adhesion to the mucous membranes of the throat, gut, etc., and adapted to release the active ingredients slowly over time in situ. These encapsulation structures may be distributed within the base material in the strip composition. In one embodiment, the encapsulation structures comprise multilamellar microparticles. The multilamellar microparticles are selected to exhibit good adhesion to the mucous membranes of the throat, and are small enough to be effectively distributed in the strip. The strips of the present invention provide the requisite pliability and tensile strength necessary to securely adhere to a person's mucosal tissues for at least one hour, more preferably at least two hours, and preferably a bioadhesive polymer is selected from the group consisting of polycarbophil, carbomer, one or more acrylic polymers, one or more polyacrylic acids, copolymers of these polymers, a water soluble salt of a co-polymer of methyl vinyl ether and maleic acid or anhydride, a combination thereof and their salts. In certain embodiments, a mucosal adhesive strip has a coated surface for resisting bioadhesion that includes at least one patterned polymer including coating layer having a plurality of features attached to or projected into a base surface. The features each have at least one microscale (<1 mm) dimension and have at least one neighboring feature having a substantially different geometry. The patterned coating layer preferably provides an average roughness factor (R) of from 4 to 50. The coating layer resists or enhances bioadhesion as compared to the base surface. An article having a surface coating with topography for controlling bioadhesion comprises a base surface, at least one patterned polymer comprising coating layer including a plurality of spaced apart features attached to or projected into the base surface which provide at least a first feature spacing distance. The features each have at least one microscale dimension and at least one neighboring feature having a substantially different geometry. The coating layer provides an average roughness factor (R) of from 2 to 50, preferably being from 4 to 50. The coating layer resists or enhances bioadhesion as compared to the base surface.

Still other embodiments include the use of bacteria that have been modified to remove or disable one or more virulence factors of the particular bacteria. In this regard, one aspect of the present invention is directed to the modification of certain human-specific pathogens by targeting one or more virulence factors thereof, preferably by using CRISPR-Cas or CRISPR-Cpf1 systems, to excise virulence factors genes, or at least portions thereof or transcriptional or translational controls therefore, such that such pathogenic pathogens are deprived of their undesired pathogenic characteristics. One of skill in the art can readily assess the number and identity of human-specific pathogens, as well as the particular virulence factors associated therewith, and can then, employing the CRISPR systems as referenced herein, remove, render incapable or otherwise disable the virulence facts of such microorganisms such that they no long pose a pathogenic threat to humans. Certain embodiments provide for the delivery, via the strips as described herein, of one or more of the following microorganisms selected from the group comprising *Lactobacillus lactis, Lactobacillus helveticus, Lactobacillus jensenii, Lactobacillus acidophilus, Lactobacillus bulgaricus, Lactobacillus amylovorus, Lactobacillus delbrueckii, Lactobacillus casei, Lactobacillus crispatus, Lactobacillus gasseri, Lactobacillus johnsonii, Lactobacillus paracasei, Lactobacillus pentosus, Lactobacillus rhamnosus, Lactobacillus curvatus, Lactobacillus plantarum, Lactobacillus brevis, Lactobacillus buchneri, Lactobacillus fructivorans, Lactobacillus hilgardii, Lactobacillus fermentum, Lactobacillus reuteri, Lactobacillus viridescens, Bifidobacterium bifidum*, and *Lactobacillus ingluviei*. The CRISPR-Cas system is preferably employed to excise the virulence factors of one or more of the following bacteria: *Lactobacillus lactis, Lactobacillus helveticus, Lactobacillus jensenii, Lactobacillus acidophilus, Lactobacillus bulgaricus, Lactobacillus amylovorus, Lactobacillus delbrueckii, Lactobacillus casei, Lactobacillus crispatus, Lactobacillus gasseri, Lactobacillus johnsonii, Lactobacillus paracasei, Lactobacillus pentosus, Lactobacillus rhamnosus, Lactobacillus curvatus, Lactobacillus plantarum, Lactobacillus brevis, Lactobacillus buchneri, Lactobacillus fructivorans, Lactobacillus hilgardii, Lactobacillus fermen turn, Lactobacillus reuteri, Lactobacillus viridescens, Bifidobacterium bifidum, Lactobacillus ingluviei* and preferably selected from the group comprising the following microorganisms deposited with the German Collection for Microorganisms and Cell Cultures where they are numbered as DSM 25972, DSM 25987, DSM 25988, DSM 25989, DSM 25973 and have been in accordance with the Budapest Treaty regarding International Recognition of the Deposition of Microorganisms for the purpose of patent deposition. In a preferred embodiment of the invention, strips containing effective amounts of these bacteria are provided that are attached to the soft palate region of a person's mouth or on other mucosal surfaces. Other LAB that may be employed in various embodiments include the following: *lactobacillus slaivarius* CICC 23174; *Lactoba-*

*cillus plantarum* CGMCC 1.557, *Lactobacillus rhamnosus* ATCC 53103, and *Lactobacillus acidophilus* ATCC 4356.

Moreover, in preferred embodiments, the microbes modified are limited to those demonstrating human tropism such that undesired and unintended changes to other animals and organisms are not affected and that the only implications of such genomic alterations of human specific pathogens are restricted to such species in a manner that is not capable of affecting other than the particular human disease at issue. This can include, for example, modifications and/or employment of integrons, which are a two-component genetic recombination system present in the chromosome of many bacterial species. The integron incorporates mobile genes termed gene cassettes into a reserved genetic site via site-specific recombination, named the Integron/gene cassette system. The integron consists of three basic elements: an integrase gene, an attachment site and a promoter. These elements can be manipulated to, for example, decrease the ability of a particular bacteria in a person's gut from being able to effectively attach to epithelial tissue; or alternatively, to coaggregate with other bacteria.

To provide necessary and sufficient written disclosure and enablement of the various embodiments of the present invention, the following references are incorporated by reference in their entireties: U.S. Pat. No. 9,017,718 to Tan; 20140065218 to Lang et. al.; U.S. Pat. Nos. 6,599,883; 8,383,201; 5,158,789; 20070218114 to Sorousch; 20040136923 to Davidson; U.S. Pat. No. 8,999,372 to Davidson; 20090196907 to Bunick; 20090196908 to Lee; 20030124178 to Haley; 20070293587 to Haley; 20100285098 to Haley; 2006-0204591 to Burrell; U.S. Pat. No. 7,087,249 to Burrelll; U.S. Pat. No. 6,210,699 to Acharya; U.S. Pat. No. 8,865,211 to Tzannis; 20140199266 to Park; U.S. Pat. No. 6,599,883 to Romeo; PCT/US2008/080362 to Dussia; 2007-0218114 to Duggan; 20040136923 to Davidson; 20110142942 to Schobel; 20040120991 to Gardner et al.; Fuchs et al. U.S. Pat. No. 4,136,162; 20040136923 to Davidson; U.S. Pat. No. 4,163,777 to Mitra; U.S. Pat. No. 5,002,970 to Eby, III; 20040096569 to Barkalow et al.; 20060035008 to Virgallito et al.; 20030031737 to Rosenbloom; U.S. Pat. No. 6,919,373 to Lam et al.; 20050196358 to Georglades et al.; U.S. Pat. No. 3,832,460 to Kosti; 2002002057 to Battey et al.; 20040228804 to Jones, et al.; U.S. Pat. No. 6,054,143 to Jones; U.S. Pat. No. 5,719,196 to Uhari; 20150150792 to Klingman; 20140333003 to Allen; 20140271867 to Myers; 20140356460 to Lutin; 20150038594 to Borges; U.S. Pat. No. 6,139,861 to Friedman; 20150216917 to Jones; 20150361436 to Hitchcock; 20150353901 to Liu; U.S. Pat. No. 9,131,884 to Holmes; 20150064138 to Lu; 20150093473 to Barrangou; 20120027786 to Gupta; 20150166641 to Goodman; 20150352023 to Berg; 20150064138 to Lu; 20150329875 to Gregory; 20150329555 to Liras; 20140199281 to Henn; US20050100559 (proctor and Gamble); 20120142548 to Corsi et al.; U.S. Pat. Nos. 6,287,610, 6,569,474, US20020009520, US20030206995, US20070054008; and U.S. Pat. No. 8,349,313 to Smith; and U.S. Pat. No. 9,011,834 to McKenzie; 20080267933 to Ohlson et. al.; 20120058094 to Blasser et. al.; U.S. Pat. No. 8,716,327 to Zhao; 20110217368 to Prakash et. al.; 20140044734 to Sverdlov et al.; 20140349405 to Sontheimer; 20140377278 to Elinav; 20140045744 to Gordon; 20130259834 to Klaenhammer; 20130157876 to Lynch; 20120276143 to O'Mahony; 20150064138 to Lu; 20090205083 to Gupta et al.; 20150132263 to Liu; and 20140068797 to Doudna; 20140255351 to Berstad et al.; 20150086581 to Li; PCT/US2014/036849 and WO 2013026000 to Bryan.

Another aspect of certain embodiments of the present invention is directed to a thin film mucosal layered strip wherein modified bacteria (e.g. via the CRISPR-Cas system) is encapsulated in a frangible enclosure and is present in an amount of at least about 0.5 ml. Other treatment agents may be encapsulated in such strips, such that antibiotics or co aggregation agents or LAB, etc. can be encapsulated in a manner that they can be released at a time when the person so desires and/or when the strip dissolves to a certain extent, e.g. when the walls of the encapsulating shell is worn thin enough to fracture to release the agent(s). The manner in which a capsule can be fractured in order to release its solvent contents is variable and will be understood by those of skill in the art. Preferably, the capsule is constructed in a manner that it is sufficiently robust such that mere transport and packaging of the strips containing such capsules does not cause any leakage or breakage of such capsules. Instead, the design of capsules is such that they are frangible with a considerable amount of force being directly applied thereto once the strips are placed on a particular mucosal surface, such as on the soft palette of a human, such that the person's tongue, when pressing against such capsule, can cause it to fracture to release the contents of the capsule. In other embodiments, two or more different materials may be released.

Short-chain fatty acid production by commensal bacteria is important in regulating the immune system in the gut. Butyrate plays a direct role in inducing the differentiation of regulatory T cells and suppressing immune responses associated with inflammation. Butyrate is normally produced by microbial fermentation of dietary fiber and plays a central role in maintaining colonic epithelial cell homeostasis and barrier function. Various embodiments described herein promote the production of butyrate via modified microbes administered to an individual, alone or in concert with the various other agents as described herein.

Preferably, the modified bacteria employed in certain embodiments of the present invention are administered orally to a patient in order to deliver the therapeutic directly to the site of inflammation in the gut. The advantage of this approach is that it avoids systemic administration of immunosuppressive drugs and delivers the therapeutic directly to the gastrointestinal tract. The viability and stability of such modified bacteria is preferably enhanced to support the production of such microbes of desired agents, e.g. tomatidine, p53 protein, etc. and by doing so, a method is provided that reduce gut inflammation, enhance gut barrier function, and/or treat autoimmune disorders. Preferably, such modified bacteria are capable of producing therapeutic anti-inflammation and/or gut barrier enhancer molecules, particularly in the presence of reactive nitrogen species, and more preferably the bacteria are functionally silent until they reach an environment containing local RNS, wherein expression of the therapeutic molecule is induced. In certain embodiments, the genetically or CRISPR engineered bacteria are non-pathogenic and may be introduced into the gut in order to reduce gut inflammation and/or enhance gut barrier function. For example, in some embodiments, the bacteria are under the control of a RNS-responsive regulatory region and a corresponding RNS-sensing transcription factor such that a desired product, e.g. butyrate, is produced, which induces the differentiation of regulatory T cells in the gut and/or promotes the barrier function of colonic epithelial cells. Use of such modified bacteria, especially those modified via CRISPR-Cas systems, provides a way to generate a desired therapeutic effect in a manner that lowers the safety issues associated with systemic exposure.

Various embodiments of the present invention are directed to the field of oncology, and in particular, embodiments directed to a method of ameliorating, treating, or preventing a malignancy in a human subject wherein the steps of the method assist or boost the immune system in eradicating cancerous cells. In certain embodiments, the administration of beneficial bacteria to an individual's microbiome is achieved, with such bacteria being modified so as to produce effective amounts of desired compositions, compounds, agents, etc., e.g. tomatidine, p53 protein, etc., to address cancerous conditions. In several embodiments, the administration of such beneficial bacteria and microbes to an individual's microbiome invokes either an active (or a passive) immune response to destroy, weaken or render less invasive certain cancerous cells. Various other embodiments are drawn to the co-administration of biological adjuvants (e.g., interleukins, cytokines, *Bacillus* Comette-Guerin, monophosphoryl lipid A, etc.) in combination with conventional therapies for treating cancer. In particular, the co-administration of various pre-biotic compositions to enhance and sustain the desired effects of the beneficial modified bacteria forms another aspect of the present invention. In this regard, incorporation by reference of U.S. Patent Publication No. 2016/0213702 to Maltzahn et al. is included as part of the written description of various aspects of the present invention. For example, in view of the fact that the microbiota of humans is complex and varies by individual depending on genetics, age, sex, stress, nutrition and diet, modifying the numbers and species of gut, oral, vaginal and skin microbiota can alter community function and interaction with the host. A number of probiotic bacteria known in the art, as well as some foods considered to be 'prebiotic' that contain substances that promote the growth of certain bacteria and that stimulate beneficial microbiota shifts to improve human health, can be employed in concert with the modified bacteria as described herein to effect desired cancer treatment regimens. For example, the administration of glycans in an amount effective to modulate the abundance of the bacterial taxa can be used to achieve better outcomes for cancer patients.

One application of the present invention is to provide a CRISPR-Cas modified bacteria, such as a lactobacteria or BCG, to a person diagnosed with cancer, so as to facilitate the production of tomatidine in a manner that is effective to preserve muscle mass and function in such individual. Other embodiments include CRISPR-Cas, CasX, CasY, etc. modified bacteria that express levels of tumor suppressor factors, such as p53, in a manner that provides an effective, therapeutic amount to an individual via the production of such factors by one or more of the individual's microbiome (e.g. gut, oral, skin, vaginal, etc.) By having the individual's microbiome responsible for administration of such factors, instead of attempting to administer such factors via more traditional routes, such as injection, pills, etc., it is believed that a better result can be attained in a much more natural fashion. Moreover, in view of the ability to further modify bacteria in various ways to provide desired factors at particular times, or in conjunction with particular agents, it is possible to fine tune the administration of desired factors, such as p53, butyrate, etc. so as to reduce any under or over production thereof. For example, rendering particular modified bacteria sensitive to a predetermined antibiotic can thus provide a way to reduce the numbers of any given modified bacteria in a manner to control the populations of such bacteria in an individual's microbiome, and hence, control the level of production of factors produced by such bacteria. To comply with written description and enablement requirements, incorporated herein by the following references are the following patent publications: U.S. Patent Publication Nos. 2014/0349405 to Sontheimer; 2014/0377278 to Elinav; 2014/0045744 to Gordon; 2013/0259834 to Klaenhammer; 2013/0157876 to Lynch; 2012/0276143 to O'Mahony; 2015/0064138 to Lu; 2009/0205083 to Gupta et al.; 2015/0132263 to Liu; and 2014/0068797 to Doudna; U.S. Pat. No. 8,945,839 to Zhang; 2014/0255351 to Berstad et al.; 2015/0086581 to Li; PCT/US2014/036849 and WO 2013026000 to Bryan; 2016/0199424 to Berry et al.; 2013/0326645 to Cost et al.; 2018/0312851 to Falb et al., 2018/0296582 to von Maltzahn et al.; 2018/0207165 to Harmsen et al., 2018/0000878 to Goodman et al. and 2018/0326008 to Schreiber et al.; Ser. No. 16/142,171 to Kovarik and Ser. No. 15/395,419 to Kovarik CRISPR-based genetic editing tools offer an efficient way to manipulate expression levels of multiple genes and to provide a solution towards the "multivariate modular metabolic engineering", to optimize the drug synthesis pathways with modular, multiplex regulation using only a few core proteins (e.g., dCas9) that are guided to specific sequences by guide RNAs.

In still other embodiments of the present invention, modifying bacteria so as to administer them to a person's microbiome is performed in a manner so that particular agents, factors or proteins derived from fungi and mushrooms, are rendered possible, with desired mushroom derived components believed to have anti-cancer characteristics, either alone or when used in conjunction with other agents. In particular, combining the referenced ability to have bacteria within a person produce desired amounts of tomatidine as well as having the same bacteria (or in other embodiments, another bacteria) produce a separate cancer-fighting agent, is one novel aspect of the present invention. In particular, by assessing initially the particular bacterial constituents of an individual's microbiome and then administering to such individual a similar species of microbe, but one which has been modified, preferably via employment of a CRISPR-Cas system, one is able to effectively administer to such individual various desired anti-cancer treatments in a way that is believed to be far less disruptive, efficient and dependable as compared to other routes of administration. The modification of specially designed bacteria that reside in a person's body is believed to alleviate the concerns regarding genetic alteration of the human genome, as what is being modified is a microbiome that is present in a person's body—but is not directly involved in the human genome itself. There are a myriad of ways to combine various triggering factors to turn on or off particular productions of agents, factors or proteins that may be included in such modified microbiome species. The present invention in various embodiments is directed to at least those embodiments where cancer therapeutic agents can be administered by the microbiome of the individual that has cancer so as to effectively treat the cancer and/or remedy the symptoms resulting from the disease.

One aspect of the present invention is directed to the employment and modification of an individual's microbiome to address muscle mass retention and as a corollary thereof, to address the counterpart of obesity by lessening the amount of fat storage by such individual. In certain embodiments, the provision of effective amounts of tomatidine is rendered available to an individual via the inoculation of the individual's microbiome (e.g. oral or gut) by particular bacteria that have been modified to express amounts of tomatidine. Still other embodiments also involve the reduction in the amount of acetate levels in an individual's body, which in turn lowers the amount of insulin the individual will produce, which has the effect of keeping fat cells from storing more energy in the form of fat. The reductions in the amount of acetate available in an individual's body further reduces the amount of the hormone ghrelin, thus reducing the hunger drive of the individual. Thus, the modification of an individual's microbiome influences various aspects of their metabolism in a manner that not only retains and maintains the ability to nurture muscle tissue, but to also reduce obesity by affecting the amount of fat that the body stores. While not bound by theory, it is believed that the gut bacteria of an individual is a substantial source of acetate production. The production of acetate by gut microbes is believed to send signals to the brain of the individual to initiate the production of insulin, conveyed via the vagus nerve. Fine tuning of the amount and type of gut microbes (e.g. via the use of antibiotics to initially reduce the kind and numbers of undesired bacteria, followed by purposeful inoculation of an individual's gut microbiome with modified microbes, e.g. via CRISPR-Cas insertion of particular factors, proteins, etc., such as tomatidine) is an effective way to address not only muscle wasting issues, but also obesity issues of individuals.

While there are many gut bacteria that produce acetate and butyrate, particular bacteria are preferably selected and even more preferably are modified using CRISPR-Cas systems to address the levels of acetate and/or butyrate production once such bacteria are introduced (or enhanced) to an individuals' microbiome. Preferably the gut microbiota are members of two bacterial divisions: the Bacteroidetes and the Firmicutes, and most preferably include *F. prausntizii*. The modification of an individual's gut microbiome is directed in a manner such that the typical increase seen in the relative abundance of the Firmicutes and a corresponding division-wide decrease in the relative abundance of the Bacteroidetes in obese individuals, is addressed. Obese people have more Firmicutes and almost 90% less Bacteroidetes than the lean people. Preferably, the administration of modified Bacteroidetes is achieved to more substantially reflect gut populations in more lean individuals, and by doing so, reducing the amount of acetate produced by the overall gut microbiome. Such a shift in the population of gut microbes to favor Bacteroidetes over Firmicutes, whether or not coupled with the administration of tomatidine, is one aspect of the present invention's objective of achieving a greater proportion of muscle mass than fat that would otherwise occur in any given individual. In still other embodiments, addressing the acetate production by especially Firmicutes, which has an increased capacity for fermenting polysaccharides relative to the lean-associated microbiome, is another way to achieve this objective, and addresses the significant obesity issues especially prevalent in Western societies.

In yet another embodiment, encapsulated structures, preferably microencapsulated structures, are employed that are filled with desired agents, including but not limited to tomatidine, butyrate, etc. and/or microbes, especially bacteria that are found in an individual's gut microbiome, such as *F. prausntizii*, such that effective amounts of the agents can be administered to treat particular diseases. Other agents may include those effective in combatting cancer, such as but not limited to tomatidine, p53 protein, statins, PTEN, rapamycin, and other agents able to treat cancer symptoms. Preferably, the bacteria comprise bacteria that are found in the communities of healthy humans, including, for example, *F. prausntizii*, *Streptococcus*, *Actinomyces*, *Veillonella*, *Fusobacterium*, *Porphromonas*, *Prevotella*, *Treponema*, *Neisseria*, *Haemophilus*, *Eubacteria*, *Lactobacterium*, *Capnocytophaga*, *Eikenella*, *Leptotrichia*, *Peptostreptococcus*, *Staphylococcus*, and *Propionibacterium*. Such encapsulated structures may be provided as strips that may be manufactured to have desired dissolvable aspects thereto and that further have encapsulated portions that house the desired agents.

Similarly, it is desired to increase the presence in samples provided to urban dwelling expectant mothers of other bacteria, and in particular, *Bacteroides-Prevotella*, *bifidobacteria*, *Desulfovibrio* spp., *Clostridium clostridiforme*, and *Faecalibacterium prausntizii*. Avoidance of antibiotics by the expectant mother during the period to which she is exposed to the various Amish soil constituents is desired if not critical in certain embodiments due to the profound changes due to such during antibiotic treatment. In other embodiments, the use of CRISPR-Cas systems is employed to increase butyrate production of these bacteria. For example, *F. prausntizii*, one of the most abundant species in the colon, is an important producer of butyrate, a major product of carbohydrate fermentation which is implicated in providing protection against colorectal cancer and ulcerative colitis.

An individual's microbiome includes the collective genomes of all the microorganisms that are part of the body's ecosystem. As stated herein, various autoimmune diseases are capable of being ameliorated by the practice of the present invention, including Crohn's disease. Prior researchers have found that several specific microbes were more prevalent in patients with Crohn's than in their healthy counterparts, while other bugs were less common in Crohn's cases. Addressing this dysbiosis, or imbalance, in the microbial ecosystem is one aspect of the present invention. In certain embodiments, certain microbiota that were known to disappear in the guts of Crohn's cases, are reintroduced, including *Faecalibacterium prausnitzii*, and at the same time, several bacteria that are known to proliferate in Crohn's cases, including those linked to IBD and colorectal cancer, are targeted to remove pathogenic abilities. In particular embodiments, providing a collection of microbes, preferably including, for example a higher than normal (e.g. that is found in any random sampling of Amish soil) amount of *Faecali*, more preferably *Enterococcusfaecalis*, is achieved to expose expectant mothers and infants thereto in order to trigger desired immune system responses. Enhancing the growth and viability of this particular bacterium in the gut—and then use of such modified bacterium to treat individuals with various diseases, such as Crohn's disease and other autoimmune diseases. Similarly, *Faecalibacterium prausnitzii*, which represent more than 5% of the bacteria in the intestine, is encouraged to populate the guts of patients. Such enhanced growth of this bacterium may also be employed to combat certain forms of inflammatory bowel disease. In various embodiments of the present invention, *Enterococcus faecalis* is are subjected to CRISPR-Cas procedures to remove undesired virulence and pathogenicity factors, such as several genes isolated from resistant enterococci (agg, gelE, ace, cyl LLS, esp, cpd, fsrB) which encode virulence factors such as the production of gelatinase and hemolysin, adherence to caco-2 and hep-2 cells, and capacity for biofilm formation. Deletion and removal of certain antibiotic resistance, for example the acquisition of vancomycin resistance by enterococci, is desired also so as to properly and safely employ this bacteria in the present invention. In a particular embodiment, the addition of *E. faecalis* LAB3 1 is employed to trigger desired immune system responses.

In certain embodiments, it may be advantageous to genetically modify a gut mucosal-associated bacteria with polynucleotides and as taught herein to express or overexpress the polynucleotides as taught herein or to produce or overproduce the polypeptides, such as butyrate and acetate, directly into the vicinity of, or within the gut mucosal barrier of a human. In a preferred embodiment, the gut mucosal-associated bacteria may by any bacteria from the species *F. prausinitzii*, *Prevotella intermedia*, and/or *Akkermansia muciniphilla*. Such overproduction may be realized by genetic modification tools involving recombinant DNA technologies, genome editing such as by using tools based on CRISPR/cas-like systems, or by classical mutation selection systems.

In an embodiment, the genetically modified host cell may be any bacteria, particularly one which is not from a species of bacteria that naturally occurs or lives in the vicinity of or within the gut mucosal barrier of a mammal. Non-limiting examples of such bacteria include any beneficial isolated intestinal bacterial strains, e.g. probiotic bacteria, particularly strains selected from the genera *Lactococcus, Lactobacillus*, or *Bifidobacterium* may be used. In addition, strict anaerobic intestinal bacteria may be used such as those belonging to the genera known to occur in the human intestinal tract. As described herein, in various embodiments, strictly anaerobic bacteria are encapsulated or microencapsulated to avoid contact with oxygen, and are delivered to a human such that the encapsulation is dissolved or fractured to release such bacteria in a portion of the body, e.g. gut, where it can thrive.

Certain embodiments employ the bacterium *Flavobacterium akiainvivens*, which was discovered in 2012 on the plant *Wikstroemia oahuensis*, or "akia," which is a flowering shrub endemic to Hawaii. That bacterium has been found on that plant and no other. The bacterium forms 2- to 3-millimeter diameter colonies that range from cream to off-white in color and wet to mucoid in viscosity, and (it) was isolated from decaying *Wikstroemia oahuensis* collected on the island of Oahu.

Certain embodiments are directed to the targeted manipulation of the gut microbiome for therapeutic applications, such as the manipulation of the gut microbiome achieved by altering the microbiota population and composition, or by modifying the functional metabolic activity of the microbiome to promote health and restore the microbiome balance. There has been recent progress in the engineering of gut commensals, which also presents great potential for biomedical applications. Specifically, in *Bacteroides thetaiotaomicron*, components for tunable gene expression were developed and characterized and expected functional outputs were observed in mice after administration of these engineered *B. thetaiotaomicron*. Thus, one aspect of various embodiments is to harness such engineered commensals, especially *F. prausntizii* for the overproduction of butyrate, for therapeutic purposes.

*F. prausntizii* was first isolated in 1922 by C. Prausnitz. Morphologically, *F. prausntizii* is a Gram-negative, non-motile and non-sporeforming rod with a diameter of 0.5 to 0.9×2.4 to 14.0 μm. *F. prausntizii* is a strictly anaerobic bacterium that produces butyrate, formate, D-lactate and $CO_2$ but no hydrogen as fermentation products and *F. prausntizii* growth is inhibited by acidic pH and bile salts. The amount of *F. prausntizii* in the healthy human gut is linked to diet. Inulin-derived prebiotics have been shown to significantly increase *F. prausntizii* concentration in the gut. *F. prausntizii* is statistically linked to eight urinary metabolites: dimethylamine, taurine, lactate, glycine, 2-hydroxyisobutyrate, glycolate, 3,5-hydroxylbenzoate and 3-aminoisobutyrate. It is believed that *F. prausntizii* has pronounced anti-inflammatory effects. While not bound by theory, *F. prausntizii* may induce an increased secretion of an anti-inflammatory cytokine interleukin 10, and a decreased secretion of pro-inflammatory cytokines like interleukin 12 and tumor necrosis factor-α production. It is further believed that *F. prausntizii* has the ability to suppress inflammation, and it is hypothesized that this is due to metabolite(s) secreted by *F. prausntizii*, including but not limited to butyrate. The number of *F. prausntizii* is significantly higher in the gut of healthy subjects as compared to IBD and it is believed that *F. prausntizii* is crucial to gut homeostasis and disease protection.

With the guidance provided herein, as well as the numerous references incorporated by reference herein, one of skill in the art will understand the feasibility of using engineered bacteria to directly manipulate the functional output of the microbiota without major modulation of the microbiota population and composition. Components in the normal diet and/or employing prebiotics and engineered probiotics are therefore harnessed to render a targeted effect on the host through modulating the functional output of the microbiome.

*F. prausntizii* is a multi-skilled commensal organism and a chief member of human microbiota. It is broadly distributed in the digestive tract of mammals and also in some insects. It is rich in the hind gut rather than in the stomach, as well as jejunum. The consumption of a higher quantity of animal meat, animal fat, sugar, processed foods, and low fiber diet (the typical westernized diet) reduces the count of *F. prausntizii*, while a high-fiber (vegetables and fruits) and low meat diet enhance the count of *F. prausntizii*. It is known to consume a variety of diet containing polysaccharides, such as the prebiotic inulin, arabinoxylans, apple pectin, oligofructose, resistant starch, fructan supplement, pectins and some host-derived carbon sources (including d-glucosamine and N-Acetyl-d-glucosamine). Meta-analyses also show that the increased consumption of fiber significantly reduces the risk of mortality.

The discovery of the clustered regularly interspaced short palindromic repeats (CRISPR) and the CRISPR-associated nuclease 9 (Cas9) system, has led to an array of strategies to manipulate the gut microbiome with precision. Engineered phage (with the CRISPR-Cas9 system) can be employed to target pathogenic bacteria, or remove a population of bacteria that aids pathogenic bacterial growth, thereby fine-tuning and restoring the balance of the gut microbiome. CRISPR/Cas9 can also be used to manipulate and differentiate genetically heterogeneous bacteria, even of the same species. Unlike conventional drugs, the CRISPR/Cas9 system targets specific bacteria at the gene level to selectively remove pathogens, virulence factors, genes of undesired expressed proteins, etc. and can further be used as an antimicrobial adjuvant to improve antibiotic treatment. Citorik et. al. demonstrated how CRISPR/Cas9 can be delivered using bacteriophages, targeting the ndm-1 gene, which codes for the broad-spectrum carbapenemase, New-Delhi metallo-β-lactamase. Ndm-1 targeting CRISPR/Cas9 specifically eliminated *E. coli* harboring the gene without affecting wild-type, or other, *E. coli* strains present in a synthetic consortium of microbes. Other examples include the re-sensitization of bacteria to antibiotics and immunization of bacteria to incoming plasmids conferring antibiotic resistance using temperate phages. Yosef et al. used CRISPR/Cas9 to target ndm-1 and ctx-M-15, which expresses a broad-spectrum beta-lactamase, and effectively selected the transduced bacteria that were antibiotic-sensitive. Thus, CRISPR/Cas9 may be employed to manipulate the gut microbiome by discriminating at the gene level to change the characteristics and functional output of the gut microbiome for therapeutic applications.

Higher consumption of fruit, vegetables, fibre and red wine has been linked to higher abundances of beneficial bacteria, including butyrate-producing *Faecalibacterium prausnitzii*. In certain embodiments, desired bacteria, such as SCFA-producers, can also be promoted by metformin. In certain embodiments, the so-called cross feeding of bacteria is encouraged to achieve desired butyrate production. For example, excess acetate produced by certain bacteria is subsequently utilized by butyrate-producing bacteria, such as *Faecalibacterium prausnitzii, Roseburia*, and *Eubacterium*, to produce butyrate. This 'cross-feeding' effect between *Bifidobacterium* and butyrate-producing bacteria ultimately leads to an increased butyrate production and augments beneficial effects, such as improvement of the gut barrier integrity and pathogen inhibition. The health-promoting attributes of butyrate-producing bacteria are supported in numerous diseased conditions, such as IBD, Crohn's disease, and ulcerative colitis, where a significant reduction of butyrate-producing bacteria is reported. Though these butyrate-producing bacteria are not directly affected by the supplementation of oligosaccharides, their butyrate production is elevated due to the increased availability of fermentative end products generated by *Bifidobacterium*. Thus, in various embodiments, prebiotics play an important role in mediating complex interactions among populations in the gut microbiota, thus presenting opportunities to achieve therapeutic approaches. Thus, in certain embodiments, a mixture of bacteria is provided in a probiotic composition to encourage such cross-feeding effect between *Bifidobacterium* and butyrate-producing bacteria, such as *F. prausntizii*. *Bifidobacterium* utilizes supplemented prebiotics, which stimulates their growth. Acetate produced by *Bifidobacterium* becomes a carbon source for the butyrate-producing microbes, stimulating their growth and butyrate-producing activities and, in turn, modulating the microbiome function and improving gut health. Similarly, provision of dietary fiber that can be metabolized by colonic bacteria into butyrate, achieves the objective of enhancing production of this desired short-chain fatty acid (SCFA), which also acts as a histone deacetylase (HDAC) inhibitor that epigenetically upregulates tumor-suppressor genes in CRC cells and anti-inflammatory genes in immune cells.

*F. prausntizii* is not detectable in the fecal samples of babies under 6 months of age (Hopkins et al., 2005.). After that, the number starts to increase gradually, and children of 1 to 2 years of age already have a significant amount of *F. prausntizii* in their GI tract. As it is believed that babies are born essentially sterile, and receive bacteria from the environment immediately upon birth, vaginally delivered infants receive their first bacteria as they pass through the birth canal and thus have microbial communities resembling those found in the vaginal microbiota of their mothers, dominated by *Lactobacillus, Prevotella* or *Sneathia* spp. Babies born by Caesarean section (C-section) don't receive vaginal microbes but instead get their first bacteria usually from the skin microbiota of their mother, dominated by taxa such as *Staphylococcus, Corynebacterium* and *Propionibacterium* spp. There is increasing evidence that the early colonization of bacteria affects the health of the infants and also influences the host health later in life. It is therefore one aspect of the present invention to provide to babies, especially those not born vaginally, with a bacterial composition that mimics what the baby would naturally experience if it were born vaginally.

*F. prausntizii* is one of the most abundant bacteria in a healthy human gut and is believed to have a positive effect on the human gut health. *F. prausntizii* belongs to the *Clostridium leptum* group (*Clostridium* cluster IV), belonging to phylum Firmicutes (Lineage: Bacteria; Firmicutes; Clostridia; Clostridiales; *Ruminococcaceae; Faecalibacterium; Faecalibacterium prausnitzii*). *F. prausntizii* has been previously called *Fusobacterium prausnitzii* (also cited as *F. prausntizii*), with it only distantly being related to Fusobacteria and more closely related to members of *Clostridium* cluster IV.

Moderate butyrate levels can prevent high-fat-diet-induced insulin insensitivity through epigenetic regulation, and mitochondrial beta-oxidation. *F. prausntizii* is one of the unique organisms that reduce various autoimmune diseases, especially type-1 diabetes via the modulation of gut epithelium homeostasis and immune system. Studies associated with gut microbiota and type-1 diabetes have a lower proportion of butyrate-producing organisms, such as Firmicutes and *Clostridium*, which protects against autoimmune diabetes. While not bound by theory, *F. prausntizii* is believed to regulate the development of autoimmune diabetes via butyrate dependent complementary pathways. An abundant quantity of butyrate can lower the gut barrier function and enhance cell apoptosis, with high levels of butyrate stimulating GLP-1 secretion and enhancing insulin sensitivity through cAMP signals, such as PKA and Epac, which inhibit gastric emptying. Due to the inhibition of gastric emptying, butyrate can be excreted slowly and accumulates, influencing the anti-inflammatory potential, pH, and oxidative stress.

Butyrate is the major product of carbohydrate fermentation in the colon. Butyrate modulates several processes and is a known anti-proliferative agent. In cultured cell lines, butyrate inhibits DNA synthesis and cell growth, mainly by inhibiting histone deacetylase. Butyrate is also suggested to regulate the citric acid cycle, fatty acid oxidation, electron transport and TNF-$\alpha$ signaling. Animal studies have indicated that butyric acid may have antineoplastic properties, which means that it may protect against colon cancer. As dietary fiber is protective against colon cancer because carbohydrates entering the large bowel stimulate the production of butyrate. Butyrate has also been suggested to provide protection against ulcerative. *F. prausntizii* is an important producer of butyrate, and the decrease of *F. prausntizii* has been correlated to lower concentrations of fecal butyrate in healthy human subjects and it is believed that *F. prausntizii* plays an important role in the protection of the colon. While not bound by theory, the benefits of butyrate are thought to depend on several aspects, such as time of exposure and butyrate amount. Increased butyrate production by *F. prausntizii* is therefore a desired outcome and employment of CRISPR systems to achieve the same, employing the known gens involved in butyrate by *F. prausntizii* is one important embodiment of the present invention.

Studies have shown that there was a statistically significant reduction in the *F. prausntizii* abundance during both fiber-free and fiber-supplemented diets, but it is postulated that the reduction during the fiber-supplemented diet was due to the use of pea fiber, which is not believed to support the growth of *F. prausntizii*, and thus, with the proper fiber being employed, the increase in butyrate production is achieved. In situations where there is insufficient fiber for the beneficial bacteria to consume, the bacteria end up eroding the mucus of the gut and leads to epithelial access by mucosal pathogens.

The relative abundance of Bacteroidetes and Firmicutes has been linked to obesity, with the Firmicutes ratio being significantly higher in obese individuals. It is believed that a high number of *F. prausntizii* leads to higher energy intake, because *F. prausntizii* is responsible for a significant proportion of fermentation of unabsorbed carbohydrates in the gut.

*F. prausntizii* cultivation has proven difficult because the bacterium is a strictly obligatory anaerobe that does not tolerate any oxygen. As described herein, encapsulation of *F. prausntizii* is achieved such that it can be effectively delivered such that the encapsulated structure can degrade or be fractured at an appropriate time and place to release such bacteria to a human to derive beneficial results, e.g. the increased production of butyrate. For example, microencapsulation, in a xanthan and gellan gum matrix, and a subsequent freeze-drying protocol can be employed to achieve this result.

Proton pump inhibitors (PPIs) are among the top 10 most widely used drugs in the world. PPI use has been associated with an increased risk of enteric infections, most notably *Clostridium difficile*. The gut microbiome plays an important role in enteric infections, by resisting or promoting colonization by pathogens. The differences between PPI users and non-users are consistently associated with changes towards a less healthy gut microbiome. These differences are in line with known changes that predispose to *C. difficile* infections and can potentially explain the increased risk of enteric infections in PPI users. On a population level, the effects of PPI are more prominent than the effects of antibiotics or other commonly used drugs. PPIs change the gut microbiome through their direct effect on stomach acid. This acidity forms one of the main defenses against the bacterial influx that accompanies ingesting food and oral mucus. PPIs reduce the acidity of the stomach, allowing more bacteria to survive this barrier. Species in the oral microbiome are more abundant in the gut microbiome of PPI users. Gastric bypass surgery compromises the stomach acid barrier and leads to gut microbiome changes similar to the PPI-associate.

Antibiotics can lead to severe changes in the gut microbiota. Antibiotics are also commonly used in treatment of IBD, even though little is known about the effects of antibiotics on gut microbiota. The fecal number of *F. prausntizii* is lowered in long treatment periods with antibiotics but it is not presently known how antibiotic resistance of *F. prausntizii* may affect human health. It is believed, however, that *F. prausntizii* has a notable impact on gut homeostasis and thus, the susceptibility of *F. prausntizii* to different antibiotics is believed to be important in the treatment of various ailments. Provision of additional *F. prausntizii* after a regimen of antibiotics is therefore one aspect of various methods of the present invention. Antibiotic-induced changes in the gut microbiota are usually temporary, but long-term microbial population fluctuations have also been reported. It is believed that antibiotics may even move the gut microbiota to a new, alternative stable state. Antibiotic-induced alterations in the gut microbiota raise the disease risk by increasing the susceptibility to pathogen colonization; for example, diarrhea caused by *Clostridium difficile* is a well-known consequence of antibiotic courses. The use of live *F. prausntizii* is preferred due to the greater immuno-stimulatory effects of live *F. prausntizii*, via TLR2 activation. It is believed that this effect is potentially linked to its barrier maintaining properties. It is butyrate, instead of other substances produced by *F. prausntizii*, that exerts significant anti-inflammatory effects observed, and it is believed that the target of butyrate is histone deacetylase 1 (HDAC1).

In other embodiments, the bacterial composition employed includes both *F. prausntizii* and *Akkermansia muciniphila*, another abundant member of the human gut microbiota. It is further believed that *Faecalibacterium prausntizii* plays a vital role in diabetes and can be used as an intervention strategy to treat dysbiosis of the gut's microbial community that is linked to the inflammation, which precedes autoimmune disease and diabetes.

The microbiota in adults is relatively stable until the persons get 60 years old. Gut alterations lead to elevated gut permeability and reduced gut mucosal immunity, contributing to the development of various cancers, autoimmune disorders, inflammatory bowel diseases, metabolic syndrome and neurodegenerative diseases. The resultant elevated intestinal permeability is a consequence of reduced expression of tight junction proteins that favors the uncontrolled passage of antigens and enables the translocation of bacterial lipopolysaccharide to the gut connective tissues and to the blood circulation, causing insulin resistance and metabolic endotoxemia.

The gastrointestinal tract pH normally ranges between 5 and 5.5 in the ileum and the colon has a range from 6.6 to 7.0, which is one of the main factors in constructing the shape of the microbial communities in the colon. Diet compositions containing fermentable polysaccharides are regulators of the intestinal pH, which facilitates a more acidic environment through the end-products of SCFAs in the gut.

Stool pH becomes more alkaline with the increase in age and differs significantly between genders with higher consumption of animal protein being one possible mechanism for higher pH. Such alkalinity is generally caused due to its alkaline metabolites produced by proteolytic putrefactive bacteria, such as *Bacteroides, Propionibacterium, Streptococcus, Clostridium, Bacillus,* and *Staphylococcus*.

An individual generally represents a unique collection of genera and sub-species and it may be different based on the diet (vegetarian or Western with high protein or fat), the age of the host organism, genetic and environmental factors. Diet greatly influences the diversity of the microbiota in the gut and the microbiota is genetically well equipped to utilize various nutritional substrates to maintain a normal gut microbiota pattern. An adequate SCFA (butyrate) production level is essential for gut integrity and butyrate-producing bacteria, such as *Eubacterium, Fusobacterium, Anaerostipes, Roseburia, Subdoligranulum,* and *Faecalibacterium*, but especially, *F. prausntizii*, have the potential of anti-inflammatory effect and help to reduce bacterial translocation, improve the organization of tight junctions and stimulate the secretion of mucin to maintain the integrity of the gut, with beneficial effects against inflammation in the gut.

Inflammation is one of the major pathophysiological factors leading to insulin resistance and progressively causes type-2 diabetes. *F. prausntizii* counts significantly decreased in diabetic individuals with negative correlation to glycated hemoglobin HbA1c values. Along with *Akkermansia muciniphila*, *F. prausntizii* is abundantly found in individuals with normal glucose tolerance compared to the pre-diabetic subjects. *F. prausntizii* can convert acetate into butyrate using butyryl-CoA: Acetate CoA-transferase (BUT) pathways, thereby providing a balanced pH in the gut.

While specific embodiments and applications of the present invention have been described, it is to be understood that the invention is not limited to the precise configuration and components disclosed herein. Various modifications, changes, and variations which will be apparent to those skilled in the art may be made in the arrangement, operation, and details of the methods and systems of the present invention disclosed herein without departing from the spirit and scope of the invention. Those skilled in the art will appreciate that the conception upon which this disclosure is based, may readily be utilized as a basis for designing of other methods and systems for carrying out the several purposes of the present invention to instruct and encourage the prevention and treatment of various human diseases. It is important, therefore, that the claims be regarded as including any such equivalent construction insofar as they do not depart from the spirit and scope of the present invention.

What is claimed is:

1. A method for reducing the likelihood of developing liver cancer in an individual diagnosed with non-alcoholic fatty liver disease, comprising:
providing in the gut of an individual a population of beneficial bacteria selected from the group consisting of *Lactobacillus* species; administering at least 6 grams per day of fiber to the individual to maintain a therapeutically effective amount of the beneficial bacteria in the gut of the individual; increasing the levels of *Roseburia*, while reducing the levels of *Akkermansia* spp. in the individual's gut microbiome, and administering an effective amount of a composition comprising modified *Lactobacillus reuteri* bacteria, wherein the *Lactobacillus reuteri* bacteria is modified using CRISPR-Cas and/or Cpf1 systems, to provide said modified *Lactobacillus reuteri* bacteria with the ability to survive conditions in the duodenum or jejunum of the individual's small intestine.

2. The method as set forth in claim 1, further comprising inhibiting expression of diacylglycerolacyltransferase-2 (DGAT-2) in said individual.

3. The method as set forth in claim 1, wherein the beneficial bacteria are present on a thin film mucosal strip.

4. The method as set forth in claim 1, wherein the population of beneficial bacteria include bacteria that have been modified to increase the level of butyrate.

5. A method for reducing the likelihood of developing liver cancer in an individual diagnosed with non-alcoholic fatty liver disease, comprising:
providing in the gut of an individual a population of beneficial bacteria selected from the group consisting of *Lactobacillus* species; administering fiber to the individual to maintain a therapeutically effective amount of the beneficial bacteria in the gut of the individual; and administering a therapeutically effective amount of a bacterial formulation comprising *Faecalibacterium prausnitzii* and at least one of *Coprococcus, Veillonella, Roseburia, Bifidobacterium*, and *Prevotella*.

6. The method of claim 5, further comprising; providing inulin in an amount sufficient to reduce the pH in the colon of the individual and acidifying of the colon to enhance intestinal Ma.sup.2+ absorption by the individual.

7. The method of claim 5, wherein the *Faecalibacterium prausnitzii* bacteria employed are from the individual treated and are first isolated from the individual's stool.

8. The method of claim 5, further comprising, employing a clustered regularly interspaced short palindromic repeats (CRISPR) CRISPR associated protein (Cas) system CRISPR/Cas to rid *Prevotella* bacteria of virulence factors selected from the group of fimbria, hemolysins, adhesions and hemagglutinins and administration of said *Prevotella* bacteria to the individual.

9. The method of claim 5, further comprising, administering a therapeutically effective amount of bacteria of the *Bacteroides* family that have been modified to reduce the amount of a ligand-activated transcription factor.

10. The method of claim 5, further comprising, increasing the proportion of *Ruminococcaceae* in the individual's gut microbiome.

11. The method of claim 5, further comprising, reducing the proportion of *Escherichia* in the individual's gut microbiome.

12. The method of claim 5, further comprising increasing the levels of *Leuconostoc, Lactococcus*, and/or *Pediococcus*.

13. The method of claim 5, further comprising, administering an effective amount of a composition comprising modified *Lactobacillus reuteri* bacteria, wherein the *Lactobacillus reuteri* bacteria is modified using CRISPR-Cas and/or Cpf1 systems, to provide said modified *Lactobacillus reuteri* bacteria with the ability to survive conditions in the duodenum or jejunum of the individual's small intestine.

14. The method of claim 5, further comprising, modifying bacteria of the *Bacteroides* family to produce reduced amounts of a ligand-activated transcription factor as compared to non-modified bacteria.

15. A method for reducing the likelihood of developing liver cancer in an individual diagnosed with non-alcoholic fatty liver disease, comprising:
providing in the gut of an individual a population of beneficial bacteria selected from the group consisting of *Lactobacillus* species; administering fiber to the individual to maintain a therapeutically effective amount of the beneficial bacteria in the gut of the individual; and administering a therapeutically effective amount of a bacterial formulation comprising *Faecalibacterium prausnitzii*, and administering an effective amount of a composition comprising modified *Lactobacillus reuteri* bacteria having the ability to survive conditions in the duodenum or jejunum of the individual's small intestine.

16. The method of claim 15, further comprising, acidifying of the colon of the individual to enhance intestinal Ma.sup.2+ absorption by the individual.

17. The method as set forth in claim 15, further comprising inhibiting expression of diacylglycerolacyltransferase-2 (DGAT-2) in said individual.

18. The method as set forth in claim 15, wherein said beneficial bacteria are encapsulated in a frangible enclosure.

19. The method as set forth in claim 15, further comprising increasing the levels of at least one of *Roseburia, Coprococcus, Veillonella, Bifidobacterium*, and *Prevotella* in the individual's gut microbiome.

20. The method as set forth in claim 15, further comprising, reducing the levels of *Akkermansia* spp. in the individual's gut microbiome.

* * * * *